United States Patent
Koerner et al.

(10) Patent No.: US 9,383,306 B2
(45) Date of Patent: Jul. 5, 2016

(54) APPARATUS AND A METHOD FOR SPECTROSCOPIC ELLIPSOMETRY, IN PARTICULAR INFRARED SPECTROSCOPIC ELLIPSOMETRY

(71) Applicant: Universität Stuttgart, Stuttgart (DE)

(72) Inventors: Klaus Koerner, Stuttgart (DE); Arnulf Roeseler, Lindow (DE); Daniel Claus, Stuttgart (DE); Wolfgang Osten, Stuttgart (DE)

(73) Assignee: Universität Stuttgart, Stuttgart (DE)

( * ) Notice: Subject to any disclaimer, the term of this patent is extended or adjusted under 35 U.S.C. 154(b) by 0 days.

(21) Appl. No.: 14/937,444

(22) Filed: Nov. 10, 2015

(65) Prior Publication Data
US 2016/0146722 A1 May 26, 2016

(30) Foreign Application Priority Data
Nov. 26, 2014 (EP) .................................. 14003984

(51) Int. Cl.
*G01J 3/447* (2006.01)
*G01N 21/21* (2006.01)
(Continued)

(52) U.S. Cl.
CPC .......... *G01N 21/211* (2013.01); *G01B 9/02091* (2013.01); *G01N 21/65* (2013.01); *G01N 2021/213* (2013.01)

(58) Field of Classification Search
CPC ..... G01N 21/211; G01N 21/21; G01N 21/65; G01J 3/02; G01J 3/447; G01J 3/18; G01J 3/42; G01B 9/02
USPC .................................. 356/327, 301, 369, 497
See application file for complete search history.

(56) References Cited

U.S. PATENT DOCUMENTS

| 4,829,186 A | 5/1989 | McLachlan et al. |
| 2002/0140938 A1 * | 10/2002 | Naya .................... G01N 21/553 356/445 |

(Continued)

FOREIGN PATENT DOCUMENTS

| DE | 288215 A5 | 3/1991 |
| DE | 288216 A5 | 3/1991 |
| DE | 102005028894 B3 | 8/2006 |

(Continued)

OTHER PUBLICATIONS

Julia Craven-Jones et al.: "Infrared hyperspectral imaging polarimeter using birefringent prisms" In: Applied Optics/ vol. 50, No. 8/ Mar. 10, 2011.

(Continued)

*Primary Examiner* — Abdullahi Nur
(74) *Attorney, Agent, or Firm* — Banner & Witcoff, Ltd.

(57) ABSTRACT

Disclosed herein is an apparatus for spectroscopic ellipsometry, preferably for infrared spectroscopic ellipsometry, and a method for spectroscopic ellipsometry employing the apparatus. In some embodiments, the apparatus may comprise a light source (12), a detector (30), a polarizer (40), an analyzer (41), and a measuring probe (10). In one embodiment, the measuring probe may comprise an ATR prism (50) having at least one first surface having at least one measuring portion (M) configured to be brought in optical contact with a measured object (72), and at least one second surface having at least one reflective portion (RX).

22 Claims, 24 Drawing Sheets

(51) Int. Cl.
*G01N 21/65* (2006.01)
*G01B 9/02* (2006.01)

(56) References Cited

U.S. PATENT DOCUMENTS

| | | |
|---|---|---|
| 2003/0030790 A1 | 2/2003 | Rakucewicz |
| 2012/0069336 A1 | 3/2012 | Rakitzis |

FOREIGN PATENT DOCUMENTS

| | | |
|---|---|---|
| DE | 102005062180 B3 | 1/2007 |
| DE | 69737818 T2 | 3/2008 |
| DE | 602004012330 T2 | 3/2009 |
| DE | 602005004771 T2 | 3/2009 |
| DE | 102012023248 A1 | 4/2014 |
| DE | 102014002514 A1 | 8/2015 |
| EP | 1491876 A1 | 12/2004 |
| EP | 1021713 B1 | 6/2007 |
| EP | 1738682 B1 | 2/2008 |
| EP | 1740951 B1 | 3/2008 |
| JP | 63-271138 A | 11/1988 |
| WO | 2009/137122 A9 | 2/2010 |

OTHER PUBLICATIONS

Michael W. Kudenov et al.: "Fourier transform channeled spectropolarimentry in the MWIR" In: Optics Express/ vol. 15, No. 20/ Oct. 1, 2007.
Parekhan M. Aljaff et al.: "Identification of Synthetic Perfume by Infrared and Optical Properties" In: Pure and Applied Chemical Sciences/vol. 1, No. 1, 19-30/ 2013.
A. Roseler: "Infrared Spectroscopic Ellipsometry" In: Akademie-Verlag, 1990.
Christoph Cobet: "Ellipsometry: A Survey of Concept" In: Springer Series in Surface Sciences 52/ DOI 10.1007 /978-3-642-40128-2_1/ Springer-Verlag Berlin Heidelberg 2014.
Hammad A. Qureshi: "Meningioma Classification using an Adaptive Discriminant Wavelet Packet Transform" In: A thesis submitted for the degree of PhD at the University of Warwick/ Oct. 6, 2009/http://go.warwick.ac.uk/wrap/2790.
Roderick D. Swift et al.: "11Hadamard transform imager and imaging spectrometer In: Applied Optics/ vol. 15, No. 6/ Jun. 1976.
Gerrit de Graaf: "Mid-Infrared Microspectrometer Systems" In: A thesis submitted for the degree of Dr. at the Technical University Delft/Dec. 1, 2008.
Yibang Zhang et al.: "Serum tumor marker detection on PEGylated lipid membrane using biosensor based on total internal reflection imaging ellipsometry" In: Elsevier B.V./ Sensors and Actuators B 159 (2011) 121-125/0925-4005/ DOI: 10.1016/j.snb.2011.06.059/ www.elsevier.com/locate/snb<http://www.elsevier.com/locate/snb>.
Yu Niu et al.: "Joint detection of tumor by markers with imaging ellipsometry biosensor" In: Elsevier B.V./ Thin Solid Films/ 0040-6090/2014/ <http://dx.doi.org/10.1016/j.tsf2014.01.043>.
WIRMS 2009: "5th International Workshop on Infrared Microscopy and Spectroscopy with Accelerator Based Sources" in Banff, Alberta, Canada, Sep. 13-17, 2009.
MSIB 2012 Workshop: "Morpho-Spectral Imaging in Biosciences" in Bordeaux, Pessac-Cedex, France, Nov. 5-6, 2012.
Dr. Reinhard Bruch: "NanoBiophotonics" Department of Physics, University of Nevada, Reno/ Feb. 27, 2007.
Jean-Charles Cigal: 11A Novel Spectroscopic Ellipsometer in the Infrared In: A thesis submitted for the degree of Dr. at the Technical University Eindhoven/Dec. 12, 2002.
Johannes Henricus Wilhelmus mentioned by Gerardus den Boer: 11Spectroscopic Infrared Ellipsometry: Components, Calibration, and Application In: A thesis submitted for the degree of Dr. at the Technical University Eindhoven/ Dec. 14, 1995.
Enric Garcia-Caurel et al.: "Advanced Mueller Ellipsometry Instrumentation and Data Analysis" In: M. Losurdo and K.Hingerl (eds.)/Ellipsometry at the Nanoscale/DOI: 10.1007 /978-3-642-33956-1_2/ Springer-Verlag Berlin Heidelberg 2013.
Enric Garcia-Caurel et al.: "Application of Fourier transform infrared ellipsometry to assess the concentration of biological molecules" In: Applied Optics/ vol. 41, No. 34/Dec. 1, 2002.
K. Hinrichs et al.: "Structure analysis of organic films by mid-infrared ellipsometry" In: Elsevier B.V./ Thin Solid Films 455-456 (2004) 266-271/0040-6090/ DOI: 10.1016/j.tsf.2004.01.011/ www.sciencedirect.com <http://www.sciencedirect.com>.
Jennifer A. Dougan et al.: "Fourier transform infrared spectroscopic imaging of live cells" In: SpectroscopyEurope/ vol. 25, No. 5/ 2013/ www.spectroscopyeurope.com <http://www.spectroscopyeurope.com>.
Ming-Hui Yang et al.: "Identification of Human Plasma Proteins by Trypsin Immobilized Digestion Chip and Electrospray Ionization Tandem Mass Spectrometry" In: Journal of Medical and Biological Engineering, 25(2): 81-86/ Apr. 18, 2015.
Marina K. Kuimova et al.: "Chemical Imaging of Live Cancer Cells in the Natural Aqueous Environment" In: Applied Spectroscopy/ vol. 63, No. 2/ 0003-7028/09/6302-0164/ 2009.
Jia Fan et al.: "Monitoring the progression of metastatic breast cancer on nanoporous silica chips" In: Philosophical Transactions of the Royal Society/ DOI: 10.1098/rsta.2011.0444/ Apr. 16, 2012 <http://rsta.royalsocietypublishings.org>.
Se-Hwa Kim et al.: „Study of Cell-Matrix Adhesion Dynamics Using Surface Plasmon Resonance Imaging Ellipsometry In: Biophysical Journal/ vol. 100, 1819-1828/ DOI: 10.1016/J.bpj.2011.01.033/ Apr. 2011.
Chuan-hui Liang: "Milieux denses, materiaux et composants" In: A thesis submitted for the degree of Dr. at the University of Caen Basse-Normandie/Nov. 28, 2013.
B. R. Wood et al.: "Progress in Fourier Transform Infrared Spectroscopic Imaging Applied to Venereal Cancer Diagnosis" In: Veterinary Pathology Online/ DOI: 10.1177 /0300985813501340/ Sep. 5, 2013 <http://vet. sagepub.com/content/early/2013/09/05/0300985813501340>.
Azzam R.M.A: "Return-path, multiple-principal-angle, internal-reflection ellipsometer for measuring IR optical properties of aqueous solutions" In: Applied Optics, Optical Society of America, Washington, DC; US; XP001556467, pp. 470-4714, Sep. 1, 2010.
Nabok et al.: "The method of total internal reflection ellipsometry for thin film characterization and sensing" In: Elsevier B.V./ Thin Solid Films/ vol. 516, No. 24/ XP025467632/ pp. 8993-9001/ Oct. 31, 2008.
Hong Fu et al.: "Retroflecting Ellipsometer for Measuring the Birefringence of Optical Disk Substrates" In: Applied Optics; Optical Society of America, Washington, DC; US; vol. 34, No. 1/ XP000486127/ pp. 31-39, Jan. 1, 1995.
Goodman T. D. et al.: "Temperature Dependence of the Birefringence of Optical-Disk Substrates" In: Applied Optics; Optical Society of America, Washington, DC; US; vol. 35, No. 16/ XP000594923/ pp. 3031-3038/ Jun. 1, 1996.

* cited by examiner

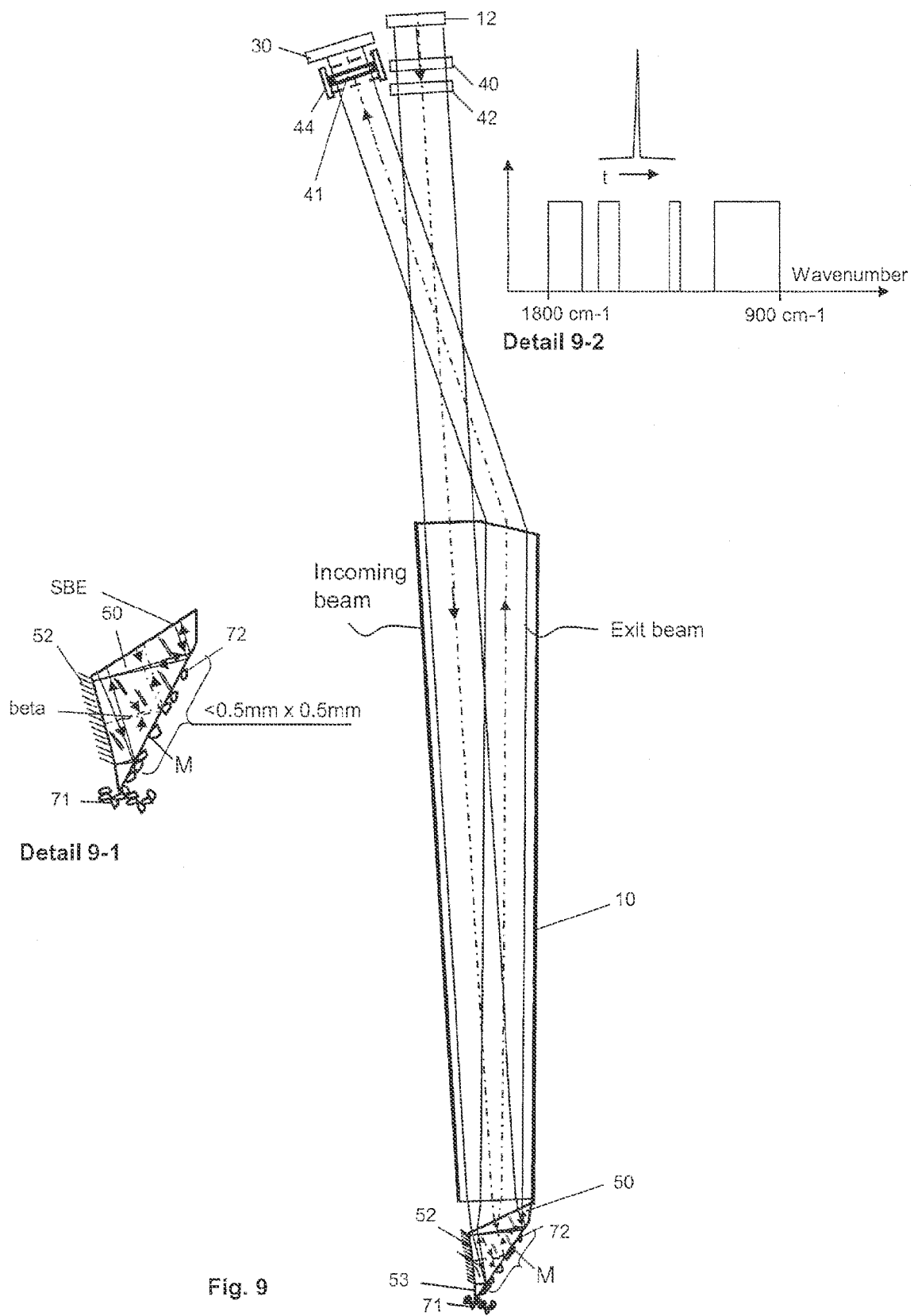

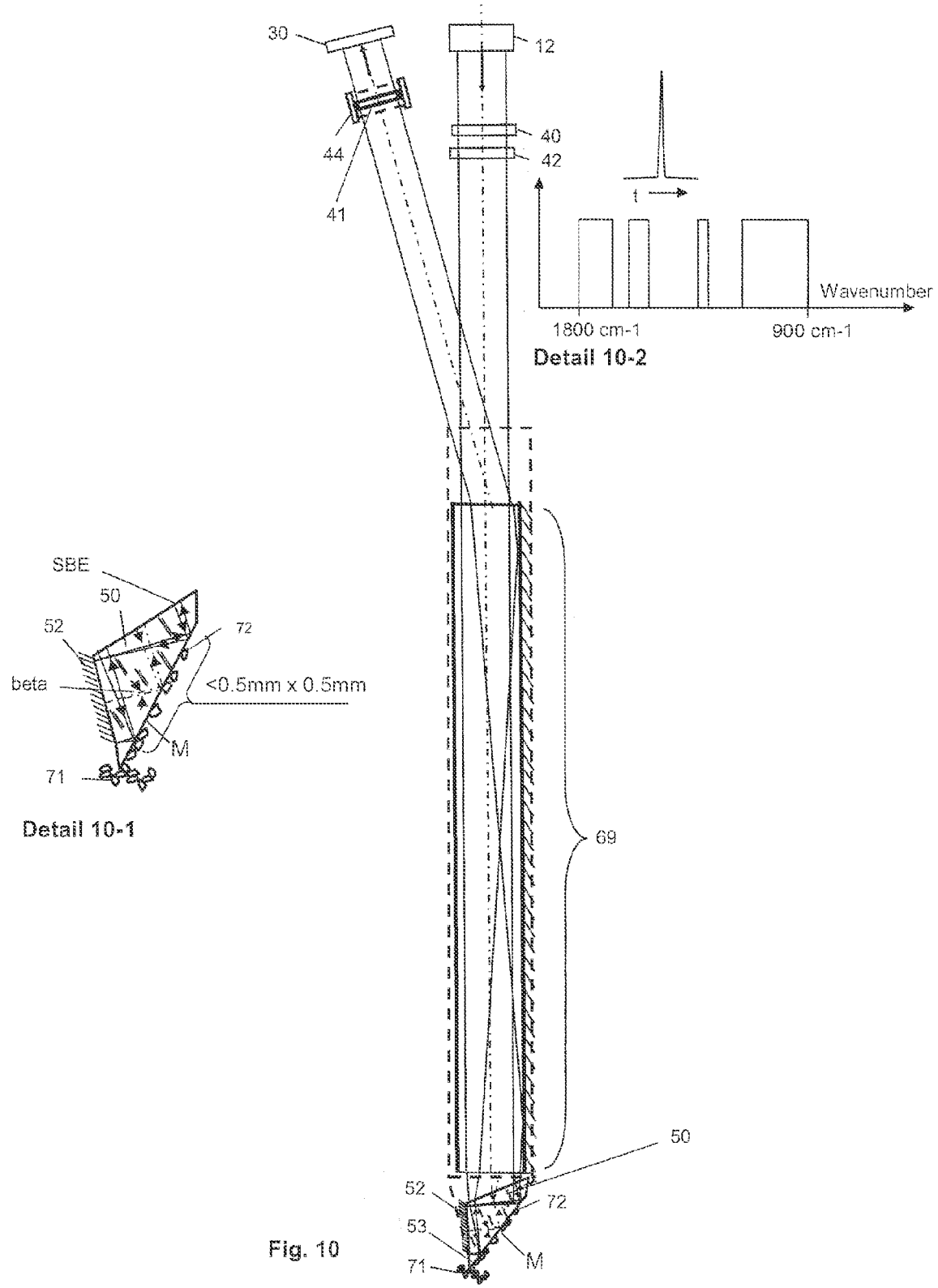

APPARATUS AND A METHOD FOR SPECTROSCOPIC ELLIPSOMETRY, IN PARTICULAR INFRARED SPECTROSCOPIC ELLIPSOMETRY

RELATED APPLICATIONS

The present application is a U.S. non-provisional filing of European Patent Application No. 14 003 984.3, filed on Nov. 26, 2014, and the present application claims priority to and the benefit of the above-identified application, which is incorporated by reference herein in its entirety.

BACKGROUND

A standard approach ("gold standard") in cancer diagnosis is a hystopathologic examination of a tissue sample in question, which is usually done by an experienced hystopathologist in a specialized laboratory. In order to carry out the examination, tissue samples are extracted from the patient by means of a biopsy. A disadvantage of this approach is that it is slow, labor-intensive and causes a considerable discomfort to the patient.

As an alternative to the hystopathologic examination, various infrared spectroscopy methods and in particular infrared Fourier spectroscopy methods for tissue analysis have been proposed. However, the majority of these methods require the extraction of a tissue sample via biopsy, usually under the application of an anesthetic. The extracted tissue sample is subsequently cut in thin slices by a microtom, the slices are further thinned and optionally dried and/or chemically treated and finally subjected to an infrared spectroscopic examination in a transmission or transflection mode. Exemplary infrared spectroscopy methods for tissue analysis are disclosed in the publication Hughes, Caryn [Thesis] Development of Fourier Transform Infrared Spectroscopy for Drug Response Analysis, University of Manchester, 2011.

R. Messerschmidt describes in WO 2009/137122 an Attenuated Total Reflection ("ATR") prism based spectroscopic method, which utilizes spectral measurements around the critical total reflection angle in infrared range by means of a Fourier transformation spectroscopy. A disadvantage of this method is that it is relatively slow, as it requires a high precision angular scan of the ATR prism and the detection and processing of many spectral images obtained at different angular positions.

Another optical approach for investigating the dielectric properties of materials and in particular of thin films is the ellipsometry. Ellipsometry can be used to measure various material properties, such as chemical composition, electrical conductivity, roughness, thickness (depth), etc. The ellipsometry is based on a detection of the changes in the polarization of reflected or transmitted light as the incident radiation (in a known state) interacts with the measured object. The polarization change may be quantified by various ellipsometric parameters, such as the tangent Psi as the square root of the intensity ratio and the phase difference Delta or a combination thereof.

Spectroscopic ellipsometry (SE) employs ellipsometric measurements of polarization changes (expressed by one or more ellipsometric parameters, such as tangent Psi and Delta), for a number of different wavelengths (or wavelength numbers). The basic principles of the infrared spectroscopic ellipsometry are described in the book of A. Roseler, "Infrared Spectroscopic Ellipsometry," Akademie-Verlag Berlin, 1990. The author has shown that from the data obtained by infrared spectroscopic ellipsometry, in particular in the mid-infrared range, valuable information about the structure and composition of various objects may be obtained.

The patent publication DE 10 2005 028 894 B3 of A. Roseler and U. Schade discloses a spectroscopic ellipsometer comprising a polarizing interferometer. The patent publication DE 10 2005 062 180 B3 of A. Roseler discloses another spectroscopic ellipsometer comprising a polarizing interferometer in which the polarizer functions as a beam splitter in the polarizing interferometer. Thus, it is possible to improve the accuracy of the measurements, even in cases of unfavorable phase difference. The patent application EP 491 876 Al of E. Garcia-Caurel, B. Drevillon and L. Schwartz discloses an infrared Fourier transformation ellipsometer for identification of biological materials and microorganisms.

An advantage of the ellipsometry is that it does not require a reference, since only the angle between different polarizations is measured. The sensitivity of ellipsometric methods, in particular spectroscopic ellipsometric methods, is very high. One disadvantage of known spectroscopic ellipsometers is that they are rather bulky and less suitable for in-vivo measurements, for example for the purposes of cancer diagnosis.

One object of the present disclosure is to provide an improved, minimally invasive spectroscopic ellipsometer which is suitable for carrying out measurements of biological and technical objects, even at greater depths in the inside of the measured object. In particular, an object of the present disclosure is to provide a minimally invasive spectroscopic ellipsometer for carrying out in-vivo measurements on human or animal tissue, preferably during a surgical intervention. Another object of the present disclosure is to improve the accuracy and reliability of spectroscopic ellipsometry measurements and to reduce the measuring time.

According to an aspect the above objects are solved by the provision of an apparatus for spectroscopic ellipsometry (spectroscopic ellipsometer) and a method for spectroscopic measurements, as defined in the independent claims, respectively. Preferred embodiments are defined in the dependent claims.

Applications of the proposed spectroscopic ellipsometer include but are not limited to in-vivo measurements on human or animal tissue or other biological objects for cancer diagnostic, diagnostic of complex metabolic processes, time resolved reaction kinetic analysis, etc. The proposed spectroscopic ellipsometer is particularly suitable for minimally invasive in-vivo measurements in the depths of the prostate, lungs, stomach, breasts and/or other human or animal organs. The measurements may be carried out during a surgical intervention such as biopsy or surgery, drug administration, tumor screening. Further applications include biological measurements of cells, tissue and/or living organisms for basic biological, medical and/or drug research; forensic, measurements of non-biological materials, etc.

Preferably, the proposed apparatus for spectroscopic ellipsometry enables reliable and traceable measurements at different spatial points of the measured object (including points in the depth of the measured object) with a lateral resolution in the sub-millimeter range. Such spatial resolution is considered to be very good for diagnostic purposes during surgery and sufficient for many other applications. For research applications, in particular under controlled laboratory conditions, the employment of brilliant light sources and diffraction limited optical arrangements, it is possible to obtain a spatial resolution in the upper two-digit micrometer range for the infrared spectral range.

According to an aspect, there is provided an apparatus for spectroscopic ellipsometry (spectroscopic ellipsometer), preferably an apparatus for infrared spectroscopic ellipsometry. The apparatus comprises a light source, a detector, a polarizer, an analyzer, and a measuring probe. The measuring probe comprises an ATR prism (Attenuated Total Reflection prism) having at least one first surface having at least one measuring portion configured to be brought in optical contact with a measured object, and at least one second surface having at least one reflective portion.

The ATR prism is configured so that:

at least a portion of polarized light entering the measuring probe undergoes an attenuated total reflection at the least one measuring portion of the first surface in optical contact with the measured object, at least a portion of the totally reflected light is reflected back towards the first surface by the at least one reflective portion of the second surface, and at least a portion of the light reflected back by the at least one reflective portion of the second surface undergoes an attenuated total reflection at the at least one measuring portion of the first surface and is decoupled from the ATR prism, wherein the difference between the magnitude of the angle (alpha_p) between the first surface and the second surface and the magnitude of the critical total reflection angle is equal or less than 12°.

The apparatus for spectroscopic ellipsometry employs a novel ATR prism (Attenuated Total Reflection prism) as an optical element for coupling the illumination light into the measured object by means of an attenuated total reflection. The term "ATR prism" is used to cover any optical element that is configured to couple and decouple infrared light into the measured object by means of an attenuated total reflection having a prism, pyramid, prism-plate or other suitable form.

The proposed ATR prism has a surface having a reflective portion thereon configured such that at least a part of the incoming light (i.e. polarized light having passed through the polarizer and optionally through a retarder and entering into the ATR prism through an optical coupling surface of the ATR prism) undergoes twice an attenuated total reflection by/at the measuring portion of the first surface in optical contact with the measured object to form an output (exiting) light, which is subsequently detected by the detector. The provision of a reflective portion for back reflection towards the measuring portion in optical contact with the object, so that the reflected light undergoes an attenuated total reflection for a second time, allows for a considerable enhancement of the measured signal. This improves the sensitivity of the measurements and reduces the measuring time. In the following the first surface, which has a measuring portion in optical contact with the measured object, where measurements are carried out by means of attenuated total reflection will be referred to as a measuring surface. The second surface, which has a reflective portion to guide the light back to the measuring portion, will be referred to as a reflective surface.

In case the ATR prism is monolithically built (i.e. built as a single optical element with fixed surfaces and angles), the provision of a reflective portion has the additional technical effect of the invariance of the average of the magnitudes of the two incident angles alpha_e1 and alpha_e2. The angle alpha_e1 is the angle of incidence of the incoming light at the measuring portion of the measuring surface, i.e. the angle between the normal to the measuring portion and the main ray of the beam of light incident on the measuring portion prior to reflection by the reflective portion of the reflective surface. The angle alpha_e2 is the angle of incidence of the light beam reflected by the reflective portion of the reflective surface at the measuring portion of the measuring surface, i.e. the angle between the normal to the measuring portion and the main ray of the beam of light reflected by the reflective portion of the reflective surface and incident on the measuring portion of the measuring surface.

In other words, the average value alpha_av, alpha_av=(alpha_e1+alpha_e2)/2, is invariant with respect to changes of each individual incident angle alpha_e1+alpha_e2.

In particular, in case of a monolithic prism with an angle alpha_p between the measuring surface and the reflective surface and more precisely between the measuring portion of the measuring surface and the reflective portion of the reflective surface, it holds alpha_p=alpha_av. Accordingly, the average value alpha_av is independent of each individual angle of incidence alpha_e1 or alpha_e2. Thus, the ATR-prism with a reflective surface provided with a reflective portion exhibits invariance of the average value alpha_av with respect to the angles of incidence alpha_e1+alpha_e2. In the following the angle alpha_p will be referred to as prism angle.

Generally, the average value alpha_av may be greater or smaller than the critical total reflection angle, wherein the difference may be equal to or lower than 12°, equal to or lower than 10°, further preferably equal to or lower than 3°. The critical total reflection angle depends on refractive index n_m of the object or medium which is to be measured and the refractive index n_p of the material forming the ATR prism (critical total reflection angle=arcsin (n_m/n_p)). The critical angle may be computed for each particular application of the spectroscopic ellipsometer. For infrared, the refractive index of the material of the ATR prism is typically in the range of 2.38 to 4.1 at the respective wavelength.

As the incident angle approaches the critical total reflection angle, the sensitivity of the spectroscopic ellipsometric measurement increases significantly. For example, the changes of the phase difference Delta as a function of the wavelength (or wavenumber) increase significantly. At the same time, however, the requirements with respect to the precision and stability of the optical arrangement increase and the angular tolerances decrease significantly. Accordingly, the angular orientation of the incident beam at the ATR measuring has to be adjusted and controlled precisely. Further, the requirements with respect to the degree and quality of collimation of the measuring light beam increase and the angular spread of the measuring beam has to be kept very small.

The proposed approach of employing an ATR prism with a reflection portion, configured such that the light undergoes a double attenuated total reflection at a measuring portion increases the robustness of the ellipsometric measurements, since the average value alpha_av of the two incident angles alpha_e1 and alpha_e2 for the first and the second attenuated total reflection is a single value invariant with respect to the changes of each individual incident angle. If for example, the first incident angle alpha_e1 for the first total reflection is reduced due to a tilt of the ATR prism or the axis of the incident light beam (for example after a change of the light source), the second incident angle alpha_e2 is automatically increased. Accordingly, the variation of the first incident angle alpha_e1 may be compensated to a certain extent, although the variation of the first incident angle may cause a considerable nonlinearity in the ellipsometry signals. This allows to guarantee and increase the stability (including the long-term stability) and robustness of the ellipsometric measurement.

Further, the variation of the incident angle alpha_e1 may be easily detected via a detection of the angle beta, which is the angle between the main ray of the light beam incident on the measuring portion of the measuring surface and the main ray of the light after double attenuated total reflection at the measuring portion of the measuring surface. Based on the measurement, a manual or automatic correction of the incident angle may be undertaken to compensate for the variation of the incident angle. The angle beta may range for example from 0° to 24°, preferably from 0° to 5°. Accordingly, the angle beta/2 may range from 0° to 12°, preferably from 0° to 2.5°. Preferably the angle beta is corrected manually or automatically, so that it is set at a small value, preferably a value under 5°, further preferably under 2°. This value enables a good coupling of the incident light beam entering the ATR prism (incoming light beam) and decoupling of the light beam that has undergone a double total reflection.

Preferably, the ATR prism angle alpha_p is adjusted to a specific value depending on the optical properties (e.g. refractive index and absorption coefficient) of expected measured object, for example expected cancer tissue. In other words, the ATR prism may be tuned for a detection of specific objects or materials, such as specific types of cancer tissue. This increases the sensitivity of the detection of these objects or materials.

Generally, the ATR prism may be configured to work at or around the critical total reflection angle. The difference between the critical total reflection angle and the angle of reflection for which the ATR prism is configured may be up to several angular degrees ($\approx 10°$), preferably approximately ±3°, more preferably approximately ±1°. Thus for example, reflection angles under the critical total reflection angle (such as for example reflection angles of up to 3° under the critical total reflection angle) may produce valuable measuring data, in particular in combination with a comparison to reference data of the measured object, which are obtained in advance (such as reference data of human tissues having known properties, such as known classification into malign or non-malign). Reflection angles above the critical angle of total reflection may assure that even if there is angular spread of the incoming beam (for example due to dispersion and/or imperfect collimation), the attenuated total reflection is assured for all portions of the incoming light beam, including the outermost rays.

In an example, a monolithic ATR prism, in particular a diamond ATR prism, can be manufactured with a high accuracy, so that the prism angle alpha_p reaches a predetermined value with a tolerance of less than $\frac{1}{10}^{th}$ angular degrees. Thus, since the prism angle alpha_p is fixed for a given ATR prism, the ellipsometric measurements can be carried out under very stable conditions, which increases the reliability and repeatability of the measurement data, even in case of unstable environment, such as for example during a surgery.

The ATR prism may have a prism, a pyramid or a conical form. In some examples, the ATR prism may be made in a plate-like or optical fiber form. The ATR prism may be arranged in an upright (vertical arrangement) or horizontal arrangement. In the upright direction, the angle between the measuring surface and a longitudinal axis of the measuring probe may be equal to or smaller than 60°, preferably equal to or smaller than 45°, more preferably equal to or smaller than 30°. This allows realizing an ATR prism having both optical and cutting function, as it will be explained in more detail below. In some examples, the ATR prism may be arranged in a horizontal arrangement with the measuring surface being parallel or near parallel to the longitudinal axis of the measuring probe.

The measuring probe may have an elongated form with a longitudinal axis that may be parallel or nearly parallel to the direction of insertion of the measuring probe. In an example, the longitudinal axis of the measuring probe may be at an angle to the insertion direction. This may facilitate the insertion of the measuring probe into the measured object. The measuring probe may have a hollow needle form, a catheter form, a hollow fiber form or any other suitable form, which facilitates the insertion of the measuring probe into the measured object (for example a living organ).

Preferably, the ATR prism and the measuring probe exhibit a diffraction limited optical design. For example the ATR prism may be miniaturized and may have cross-sectional dimensions of about 1 mm×1 mm, preferably 0.5 mm×0.5 mm. The lateral extension of the measuring probe (i.e. the cross section of the measuring probe) may be about 2 mm×2 mm, preferably about 1 mm×1 mm, most preferably around 0.2 mm×0.2 mm. This reduces the damages caused to the measured object and enables spatial measurements at relatively high spatial resolution.

The number of reflections at the reflective surface may be more than one. Generally, the number of reflections is uneven (i.e. 2n+1, with n=1, 2, 3, . . . ). In this case, it is possible to assure that the average angle alpha_av exhibits invariance with respect to each individual incident angle, as described above for the case of one reflection.

The remaining components of the apparatus for spectroscopic ellipsometry, such as a light source, analyzer, polarizer, detector, etc. may be arranged in a known manner. Preferably the apparatus for spectroscopic ellipsometry is a Fourier spectroscopic ellipsometer.

The apparatus for spectroscopic ellipsometry may further comprise a suitable data processor for processing the detected spectral ellipsometry data, for example to determine one or more ellipsometric parameters as a function of the wavelength (or wavenumber). Based on the obtained spectroscopic ellipsometric parameters one or more characteristics of the measured object (such as the complex refractive index) may be determined. Further, an unknown object may be identified or classified by for example comparing the obtained characteristics with reference characteristics.

In the apparatus for spectroscopic ellipsometry, the first surface (measuring surface) and the second surface (reflective surface) may intersect along a common line of intersection, thereby forming a cutting blade for cutting through the measured object. Alternatively, the ATR prism may comprise a cutting blade (cutting portion) for cutting through the measured object. In both cases, the cutting blade may form the tip of the measuring probe that is first inserted into the measured object. Preferably, the cutting angle is equal to or lower than 60°, preferably equal to or lower than 45°, further preferably equal to or lower than 30°.

In the first case, the cutting angle of the cutting blade is equal to the prism angle alpha_p, which is selected such that there is a double attenuated total reflection on the measuring surface and which depends on the refractive index of the ATR prism material and the refractive index of the measured object. Depending on the material of the prism, this may prevent the realization of very sharp cutting blades. One advantage of this arrangement may be that at least one cutting surface or a part thereof may serve as a measuring portion, thereby allowing spectroscopic measurements also at object positions close to or in immediate vicinity of the cutting portion. Thus, the zone around the tip or front end of the measuring probe not accessible to measuring light may be reduced or altogether eliminated, thereby allowing optical measurements in the depth of the measured object.

In the latter case, the ATR prism is formed with a cutting blade with a freely selectable cutting angle. The cutting blade may be made of a non-transparent hart material, which is suitable for cutting through the measured object (such as stainless steel). Preferably, the cutting blade is made of an optically transparent material, such as for example diamond, ZnSe, crystalline silicon, crystalline germanium, etc. Further preferably the ATR prism with the cutting blade has a monolithic structure, i.e. the cutting blade is has fixed mechanical (and in case of transparent blade optical) contact with the remaining, optically active part of the ATR prism. The cutting surfaces of the cutting blade may be in flush with the first and the second surfaces of the ATR prism, respectively (i.e. with the measuring and the reflective surface of the ATR prism, respectively).

One advantage of an ATR prism comprising a cutting blade which is not formed by an intersection of the measuring an the reflective surface (i.e. a cutting blade formed as an element different in its construction than the optically active part of the ATR prism) is that the cutting angle of the cutting blade may be more freely set than the prism angle (which depends on the critical total reflection angle). In particular, the cutting angle (i.e. the angle between the cutting surfaces constituting the cutting blade) may be considerably lower than the prism angle (i.e. the angel between the measuring and the reflective surfaces). Thus, the cutting angle may be preferably equal to or less than 30°, more preferably equal to or less than 25°.

This facilitates the cutting through the measured object and reduces the destructions and injuries induced during insertion of the probe in the measured object. However, in this case parts of the measured objects around the cutting blade may not be accessible to the measuring light.

In both of the above described examples, the ATR has a double function: an optical and a cutting function. An advantage of an ATR prism having a double function is that the optical measurement may be performed in-situ, immediately after the cutting of the measured object. In case of soft tissues and other similar materials, as a rule a thin fluid film or layer is formed on the measuring surface of the ATR prism while the ATR prism (with or without additional cutting blade) cuts through the soft tissue. Due to this thin fluid film or layer, there is a good optical coupling between the cut part of the tissue that is to be measured and the measuring surface. Accordingly, it is not necessary to apply additional high pressure, in order to assure good optical contact. This is a considerable advantage over a horizontal ATR approach, which generally requires the application of high pressure in order to ensure good optical contact between the horizontal measuring surface and the measured object, in particular in case the examined soft tissue has been previously cut by a microtome and the drying process of the cut tissue has already started.

The optically active part of the ATR prism and optionally the whole ATR prism may be made of any suitable optical material that has a sufficient transparency in the relevant spectral range (for example infrared). For example the ATR prism may be made of diamond, zinc selenite (ZnSe), crystalline germanium (Ge), crystalline silicon (e.g. produced by a floating zone process), etc.

In an example, the ATR prism (with the cutting blade) is made of diamond. Diamond is optically transparent for a broad spectral range, has a high refractive index, in particularly in infrared range, and exhibits an excellent durability, chemical inertness and biocompatibility. Due to its high hardness, it allows realizing an ATR prism having a double function: an optical and a cutting function for cutting through the measured object. Further, it is possible to manufacture very small ATR prisms with a high precision. This facilitates the manufacturing of very thin, minimally invasive measuring probes.

Crystalline silicon (Si) also exhibits high hardness and good biocompatibility. An additional advantage is that it has a high refractive index ($n=3.4$ in infrared), thereby enabling the construction of ATR prisms with very sharp cutting blades having cutting angles equal to or less than 30°. Further, due to the high refractive index, a silicon surface behaves almost like a perfect mirror surface when the angle of incidence is greater than about 60° (total reflection without attenuation or non-attenuated total reflection). This effect may be advantageously used to guide a polarized infrared light coupled to the ATR prism to the measuring portion of the measuring surface.

Crystalline germanium (Ge) has also a very high refractive index in infrared ($n=4$ for mid infrared range). This allows constructing ATR prisms with very sharp cutting blades having cutting angles equal to or less than 25°. Further, as in case of crystalline silicon, it allows to advantageously use the mirror like behavior at high incident angles (for example higher than) 50°, to guide the light coupled to the ATR prism to the measuring portion of the measuring surface.

For example, the first and/or the second surface may comprise at least one reflective portion, configured to reflect incident light by means of non-attenuated total reflection towards the second surface. Thus, it is possible to easily realize an optical guide like structure without the application of a reflective layer, thereby reducing the costs of the ATR prism and simplifying the production.

Of course, the first and/or the second surface may comprise at least one reflective region provided with a reflective layer. The reflective layer may be for example a metal layer, such as an aluminum layer. The reflective layer may have a multilayer structure, preferably with a hard coating layer as an outermost layer.

In an example, the first surface may comprise a plurality of measuring portions, each of them configured to be brought into optical contact with the measured object. This improves the detected measurement signal and enables reducing the measurement time. However, the lateral spatial resolution may be reduced, since the measurement signal is collected from different spatially distant sites.

In an example, the ATR prism may comprise a plurality of surfaces, each having at least one measuring portion configured to be brought in optical contact with a measured object. The apparatus for spectroscopic ellipsometry may also comprise a plurality of surfaces, each having at least one reflective portion. In an example, the reflective portions may be provided on each of the surfaces comprising the at least one measuring portion.

For example, the ATR prism may exhibit a pyramid form and the pyramid faces may have at least one measuring portion and at least one reflective portion, arranged such that there an attenuated total reflection occurs twice at each measuring portion provided on each of the pyramid faces. Thus, it is possible to realize a very compact multi-channel ATR prism that is capable of simultaneously measuring the spectroscopic polarization properties at at least two different sites of the measured object. At the same time the pyramid faces meeting at the apex of the pyramid may serve as cutting surfaces for cutting through the measured object.

In some examples, the number of reflections at each reflective surface may be one. The number of reflections at the reflective surfaces may be more than one, for example three, five, etc.

The spectroscopic ellipsometric measurement may be combined with further optical measurements, all of them using advantageously the same ATR prism as an optical coupling element. To this end the ATR prism may comprise a plurality of optical coupling surfaces. The ATR prism may comprise a first optical coupling surface for coupling light (polarized light) for the spectroscopic ellipsometric measurement into the ATR prism and optionally decoupling the light after an interaction with the object out of the ATR prism. The ATR prism may further comprise one additional (second) optical coupling surface for coupling light for further optical measurements into the ATR prism (and optionally decoupling the light for further optical measurements after interaction with the measured object out of the ATR prism). The further optical measurement may include but is not limited to any of Raman spectroscopy, optical coherence tomography, swept-source spectral-domain optical coherence tomography, microscopic observation (preferably in ultraviolet, visible or near infrared light).

For example, the spectroscopic ellipsometric measurement may be combined with Raman spectroscopy measurement. Preferably, the ATR prism is configured such that the Raman excitation light emitted by a suitable light source (for example light source emitting light in the near infrared (NIR), visible (VIS) or ultraviolet (UV) range) passes through the second coupling surface and is directed to the measuring surface of the measuring probe. The scattered Raman light may exit the ATR prism through the second coupling surface or through a respective exit surface for the Raman scattered light and be directed to a suitable detection path for the Raman spectroscopy.

Similarly, it is possible to combine the spectroscopic ellipsometric measurement with other measurements, such as optical coherence tomography (in particular swept-source spectral-domain optical coherence tomography), microscopic observation (preferably in visible or near infrared light) or any other optical measurements. The ATR prism may comprise more than two optical coupling surfaces for the different types of optical measurements.

The optical coupling surfaces may be plane or curved surfaces (for example convex or concave curved spherical or aspherical surface). Preferably, the measuring probe and the ATR prism are configured such that the light for further optical measurement is incident normally or near normally on the measuring portion of the measuring surface. For example, the at least one optical coupling surface for coupling light for further optical measurement may be arranged such that this surface or a tangential plane to this surface is normal or nearly normal with respect to the measuring surface. Nearly normal incidence means incidence at an angle deviating from the normal (perpendicular) incidence by no more than ±15°, preferably by no more than ±12°. Due to the normal or near normal incidence of the light for further optical measurement to the measuring portion of the measuring surface, this light does not experience a total reflection, so that the photons returned from the measured object may pass through the measuring surface and be directed towards a suitable detector (i.e. directed in a suitable detection path for second optical measurement).

The apparatus for spectroscopic ellipsometry may comprise additional light sources (such as additional light sources for Raman excitation light, optical coherence tomography light and/or microscopic observation light), detectors and additional optical forming additional illumination and detection paths. Thus, it is possible to combine at least two different optical sensors in the same optical arrangement and to carry out further optical measurements, preferably simultaneously with the spectroscopic ellipsometric measurements. The detected data of the different optical measurements may be combined and used to determine the properties of the measured object. This may for example improve considerably the identification of unknown objects, for example the classification of an observed tissue as healthy tissue, cancer tissue, etc.

The apparatus for spectroscopic ellipsometry may comprise a kit or a magazine of measuring probes, wherein preferably each of the probes exhibits an ATR prism with different prism angle (i.e. different angle between the measuring and the reflective surface). The different probes may be easily exchanged when the need arises. In an embodiment, due to the invariance of the average value alpha_av, the alignment of the optical system after a change of the measuring probe is relatively simple and may be carried out automatically.

The apparatus for spectroscopic ellipsometry may employ different light sources, such as broadband light sources emitting light with a substantially continuous spectrum or broadband light sources emitting monochromatic or quasi-monochromatic light with a variable (i.e. scannable) wavelength within a broad spectral range (e.g. so called swept sources). The emitted monochromatic or quasi-monochromatic light may be frequency and/or amplitude modulated. The broadband light source may be combined with a monochromator, a spectrometer or an interferometer, as in known in the art.

The broadband light source may be for example a brilliant light source, such as a synchrotron radiator (emitting preferably in mid-infrared), a broadband quantum cascade laser or a laser battery. Through the use of such brilliant light sources, it is possible to achieve a diffraction limited optical design and miniaturize the measuring probe. Further, the overall measuring time may be reduced. This facilitates the application of the spectroscopic ellipsometer for in-vivo tissue analysis, for example during a surgical intervention.

If quantum cascade lasers or other laser sources are used, it is preferable to reduce the time coherence of the illumination light. This reduces or prevents the occurrence of parasitic interferences causing errors in the ATR spectroscopic measurements.

The spectrometer may be any conventional spectrometer, for example a conventional infrared Fourier transform spectrometer. An exemplary spectrometer is disclosed for example in DE 10 2014 002 514. The interferometer may be for example a Michelson-interferometer, a rotatable-mirrors based interferometer or any other suitable interferometer. Preferably, the apparatus for spectroscopic ellipsometry is a Fourier spectroscopic ellipsometer.

The detector may be an integral detector, for example a spatially and/or spectrally integrally detecting detector. The detector may be a one or two-dimensional detector array with a plurality of detector elements. Suitable detectors for light in the infrared spectral range are for example mercury-cadmium telluride (MCT) detectors. Suitable detectors for light in the visible range are for example CCD cameras.

Further, the apparatus for spectroscopic ellipsometry may comprise a data analysis component configured to process the obtained spectroscopic ellipsometer data to obtain one or more ellipsometric parameters as a function of the wavelength (or wavenumber) of the illumination light. The ellipsometric parameters may include tangent Psi and Delta (tangent Psi is the square root of the intensity ratio and Delta is the phase difference) or a combination thereof, each as a function of the wavelength (or wavenumber) of the illumination light. The analysis may include a Fourier transform spectrometric analysis or any other suitable analysis. Further, the analysis may comprise a Principal Component Analysis or other suitable statistical analysis to obtain characteristic features, which may be then used to identify or classify an unknown measured object. Research carried out by the inventors on tissue samples has shown that based on the obtained ellipsometric data (in particular infrared ellipsometric data) significant information concerning the bio-molecular composition of the tissue sample may be obtained.

According to a further aspect, there is provided a method for spectroscopic ellipsometric measurement by using the apparatus for spectroscopic ellipsometry according to an aspect of the present disclosure. The method comprises:

bringing the at least one measuring portion of the first surface in optical contact with the measured object;

illuminating the at least one measuring portion with incident light, so that at least a portion of the incident light undergoes an attenuated total reflection by the at least one measuring portion, reflecting, by the at least one reflective portion of the second surface, at least a portion of the totally reflected light back towards the measuring portion, whereby at least a portion of the light reflected back by the reflective portion undergoes an attenuated total reflection by the at least one measuring portion of the first surface;

decoupling the totally reflected light from the ATR prism, detecting at least a portion of the light exiting the ATR prism; and determining at least one ellipsometric parameter as a function of the wavelength of the incident light.

As explained above, after having passed through a polarizer and optionally a retarder the polarized incoming light is coupled to the ATR prism, where it undergoes twice an attenuated total reflection on the boundary between the measuring portion of the measuring surface of the ATR prism and the measured object. The light exiting the ATR prism may pass through an analyzer and optionally a retarder and/or further optical elements (such as filters, lenses, etc.) prior to being detected and subjected to further analysis to obtain ellipsometric parameters (e.g. Delta, tangent Psi or a combination thereof) as a function of the wavelength (or wavenumber) of the illumination light, as known in the art. The ellipsometric measurements may be carried out for a plurality of angular positions (preferably at 0°, 45°, 90° and 135°) of the analyzer with respect to the polarizer.

The analysis of the obtained spectroscopic ellipsometric data may include a Fourier transform spectrometric analysis or any other suitable analysis. Research carried out by the inventors on tissue samples has shown that based on the obtained ellipsometric data (in particular infrared ellipsometric data) significant information concerning the bio-molecular composition of the tissue sample may be obtained.

The ellipsometric measurements may be repeated for a plurality of different measurement sites or regions in and/or on the measured object. Thus, the method for spectroscopic ellipsometry may include moving the measuring probe to a new region or new measurement site of the measured object and repeating the steps of bringing the at least one measuring portion of the measuring surface in optical contact with the measured object, illuminating the at least one measuring portion, reflecting, by the at least one reflective portion of the reflective surface, at least a portion of the totally reflected light back towards the measuring portion of the measuring surface, where it undergoes a second attenuated total reflection, decoupling the totally reflected light from the ATR prism and detecting at least a portion of the exiting light.

By repositioning the probe (i.e. spatially translating the probe), it is possible to conduct a multiple measurement at a plurality of spatially separated points within and/or on the measured object, so as to obtain a spatial scan of the ellipsometric parameters as a function of the wavelength (or wavenumber). The distance between the measuring points (i.e. the density of the spatial measurements) as well as their arrangement may be freely selected according to the specific application. Since the measuring probe and more specifically the ATR prism may be miniaturized, the spatial resolution of the scan may be very relatively high, for example in the sub-millimeter range down to two-digit micrometer range.

Based on the obtained data, it is possible to determine the two- or three dimensional spatial distribution of the refractive index "n" and the absorption coefficient "k" (i.e. the imaginary part of the complex refractive index) of many different objects, such as for example living organs. The obtained information is much richer than the information obtained solely on the basis of spectroscopic measurements (for example spectroscopic absorption measurements).

The spectroscopic ellipsometric measurement may be combined with further optical measurements, all of them using advantageously the same ATR prism.

For example, the spectroscopic ellipsometric measurement may be combined with Raman spectroscopy measurement. The method may comprise illuminating at least one portion of the measuring surface of the ATR prism in contact with the measured object with Raman excitation light, wherein the Raman excitation light is incident on the illuminated portion perpendicularly (normally) or at an angle deviating from the perpendicular (normal incidence) by no more than ±15°, preferably by no more than ±12°; detecting at least a portion of the Raman scattered light and subjecting the detected light to a Raman spectroscopy analysis.

The Raman excitation light may be emitted by a suitable light source (for example a light source emitting light in the near infrared (NI), visible (VIS) and ultraviolet (UV) range) and be coupled into a Raman spectroscopy illumination path including the ATR prism. Due to the normal or near normal incidence of the Raman excitation light to the measuring portion for Raman spectroscopy of the measuring surface, the incident Raman excitation light does not experience a total reflection, so that the excited Raman photons may pass through the measuring surface and be directed towards a suitable detector for scattered Raman light (i.e. directed in a suitable detection path for the Raman spectroscopy). The Raman spectroscopy illumination and/or detection paths may have further common components with the spectroscopic ellipsometry illumination and detection path (other than the ATR prism).

It is also possible to combine the spectroscopic ellipsometric measurement with optical coherence tomography measurements, in particular swept-source spectral-domain optical coherence tomography. The method may comprise illuminating at least one portion of the measuring surface of the ATR prism in contact with the measured object with optical coherence tomography illumination light, wherein the optical coherence tomography illumination light is incident on the illuminated portion perpendicularly (normally) or at an angle deviating from the perpendicular (normal) incidence by no more than ±15°, preferably by no more than ±12'; detecting at least a portion of the light returned back from the measured object and subjecting the detected light to an optical coherence tomography analysis.

Due to the normal or near normal incidence of the optical coherence tomography illumination light (for example an illumination light in the visible (VIS) or near infrared (NI) spectral range) to the measuring surface, the incident optical coherence tomography illumination light does not experience a total reflection, so that the light returned back from the measured object may pass the measuring surface and be directed in the direction of a suitable detector for the optical coherence tomography light (i.e. directed in a suitable detection path for the optical coherence tomography).

Still further it is possible to combine the spectroscopic ellipsometry measurements with microscopic observation of the measured object, for example in the visible spectral range, in the near infrared spectral range or in the ultraviolet spectral range. In this case the ATR prism and the measuring surface of the ATR prism may be used in the illumination and detection path of the microscopic system. This allows observations of the measured objects on a microscopic scale, while carrying out spectroscopic ellipsometry measurements. Further it is also possible to carry out image processing on a microscopic scale, preferably in real-time, for example to control the progress of a surgical intervention.

The method may comprise illuminating the at least one portion of the measuring surface of the ATR prism in contact with the measured object with illumination light in the visible spectral range, wherein the illumination light is incident on the illuminated portion perpendicularly (normally) or at an angle deviating from the perpendicular (normal) incidence by no more than ±15°, preferably by no more than ±12°, detecting at least a portion of the light returned back by the measured object, thereby forming a microscopic image of the measured object.

A combination with other optical sensors and optical measurement methods is also possible.

In the above examples, it is possible to obtain data by a plurality of different optical measuring method from a substantially the same measuring site of the object. In this case the illuminated portion of the measuring surface for further optical measurement may overlap at least partially with the measuring portion for infrared spectroscopic measurement by double attenuated total reflection. However, it is also possible to provide an ATR prism, in which the different optical measuring methods use different portions of the measuring surface. For example, the measuring portion for the attenuated total reflection infrared spectroscopic measurement may not coincide with the area used for the additional optical measurements. Further, in the above examples, it is not necessary that the light used for the additional optical measurements uses the whole area of the measuring portion used by the attenuated total reflection infrared spectroscopic measurement.

The above and other objects, features and advantages of the present disclosure will become more apparent upon reading of the following detailed description of preferred embodiments and accompanying drawings. Other features and advantages of the subject-matter described herein will be apparent from the description and the drawings and from the claims. It should be understood that even though embodiments are separately described, single features thereof may be combined to additional embodiments.

BRIEF DESCRIPTION OF THE DRAWINGS

These and other objects, features, aspects, and advantage of the present disclosure will become better understood with regard to the following description, claims, and drawings. The present disclosure is illustrated by way of example, and not limited by, the accompanying figures in which like numerals indicate similar elements. Moreover, a list of reference numerals and corresponding explanations are provided in Table I.

FIG. 9 shows an exemplary ATR prism;

FIG. 10 shows an exemplary apparatus for infrared spectroscopic ellipsometry;

DETAILED DESCRIPTION

Throughout the present application, the term "light" is used to mean any electromagnetic radiation from terahertz to deep ultraviolet range. The term "infrared light" is used to mean electromagnetic radiation in the near (NIR), mid (MIR) and far infrared range (FIR).

The figures are schematic representation, which are not up to scale and which may comprise parts that are enlarged or downsized for a better understanding. Further some parts may be omitted for better understanding.

Figure 1:
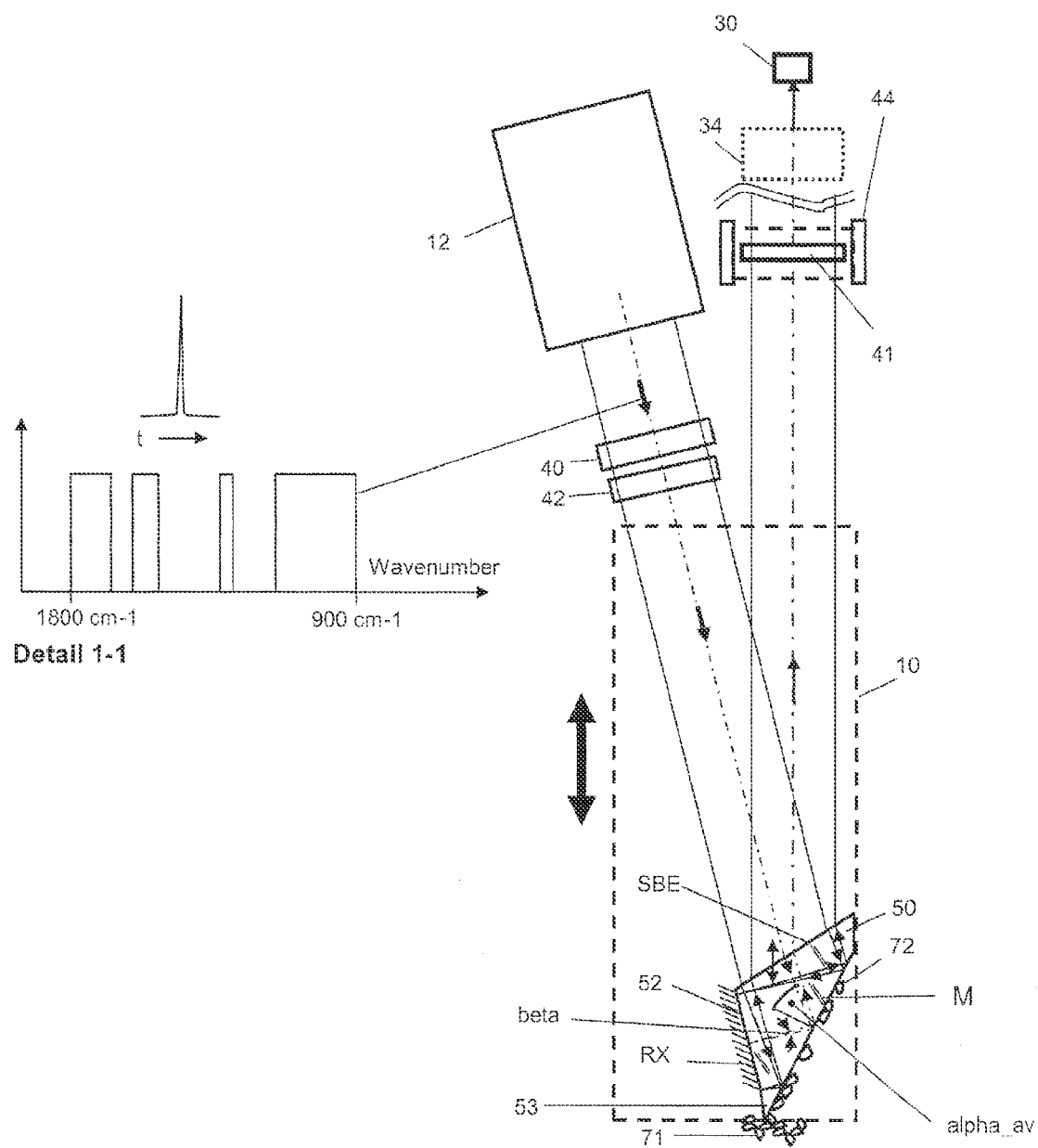
FIGS. 1 to 4 show exemplary apparatuses for infrared spectroscopic ellipsometry.

FIG. 1 shows schematically the optical layout of an apparatus for infrared spectroscopic ellipsometry (spectroscopic ellipsometer) according to a first example. The spectroscopic ellipsometer may be used for cancer and/or metabolism diagnosis.

The spectroscopic ellipsometer comprises a quantum cascade laser battery 12 with a variable (scannable) wavelength as an infrared light source (so called swept source). The wavelength/wavenumber of the light emitted from the laser battery may be swept or scanned in time over a broad spectral range, for example from 900 $cm^{-1}$ to 1800 $cm^{-1}$ (swept source). Preferably, it is possible to select out of the broad spectral range and optionally address (for example by amplitude and/or phase modulation) individual spectral bands known as producing spectral information relevant for cancer and/or metabolism diagnosis. The spectroscopic ellipsometry measurements are then carried out for the selected spectral bands. This reduces the radiation damage of the measured object and the overall measurement time. Detail 1-1 shows the spectrum of the emitted infrared light with a number of selected spectral bands that are scanned with the time t.

The selected spectral bands are serially scanned in time (for example starting from the higher wavenumber in the direction of the lower wavenumbers), wherein the scanning resolution is preferably at least 1 $cm^{-1}$ and the spectral full width at half maximum of each scanned laser line is lower than 1 $cm^{-1}$.

The light emitted from the laser battery 12 is collimated by a suitable collimator (not shown) and is coupled into a conventional ellipsometric illumination path comprising a 45° polarizer 40 and a retarder (compensator) 42. The retarder (compensator) 42 facilitates the measurement of small phase differences, i.e. small phase angles. The detection path of the spectroscopic ellipsometer comprises an analyzer 41 coupled to a computer controlled rotary stage 44. Measuring positions of the rotary stage 44 may be 0°, 45°, 90° and 135°, preferably with an angular tolerance of or lower than 0.05°. Other measuring positions are also possible. The detection path comprises further a suitable detector 30 for infrared light with corresponding optical system 34. The detector may be a spatially and/or spectrally integrally detecting MIR detector, such as a mercury-cadmium telluride (MCT) detector. The selected spectral bands shown in Detail 1-1 are scanted at each angular position of the rotary stage 44 with the analyzer 41 and spectroscopic ellipsometric information collected by the detector.

After having passed through the polarizer 40 and the retarder 42, the polarized illumination light is coupled into a measuring probe 10. The measuring probe 10 exhibits an elongated form and may be formed as a hollow needle or a catheter with a maximal cross-section of about 2 mm×2 mm, preferably about 0.6 mm×0.6 mm. The longitudinal axis LA of the elongated measuring probe 10 may be generally parallel to the direction of insertion of the measuring probe into the measured object identified in FIG. 1 by a double-sided arrow (upright arrangement).

The measuring probe 10 may be connected to a suitable computerized mechanical driving mechanism (not shown in FIG. 1) that inserts the measuring probe 10 into the measured object (for example, a human or animal organ). To assist the insertion of the measuring probe 10 into the measured object, the measuring probe may be subjected to micro-vibrations, for example up and down vibrations in the direction of insertion of the measuring probe 10. The micro-vibrations may be ultrasonic micro-vibrations.

The measuring probe comprises an ATR prism 50 positioned in a housing made of stainless steel or other suitable biocompatible material. In the hosing further optical elements as a part of the illumination and/or detection path may be arranged. The further optical elements (not shown in FIG. 1) may for example comprise an optical fiber, mirrors, lenses and other suitable elements. Further, in the housing mechanical and/or electrical elements adapted to secure the ATR prism in place and connect the measuring probe (mechanically and/or electrically) to the mechanical driving mechanism and/or a suitable controller may be arranged.

The ATR prism 50 is arranged at the tip of the measuring probe 10. The ATR prism 50 is made of a diamond and has a diamond cutting blade 53 at its tip. The cutting blade 53 has a cutting angle of preferably about 41°. The cutting surfaces of the cutting blade 53 contact the measuring surface and the reflective surface, respectively. In other words, the optically active part of the ATR prism 50 and the cutting blade 53 form one integral, monolithic element made of diamond. Thus, the ATR prism 50 has both an optical function (coupling polarized light into the measured object by means of attenuated total reflection and optionally geometric-optical separation of the illumination and detection light paths, respectively incoming and exiting light beams) and a cutting function (cutting through the measured object, for example human tissue). The ATR prism 50 may be subjected to micro vibrations, in order to assist the cutting process and reduce the collateral tissue damage.

The ATR prism 50 has an optical coupling surface SBE, through which the illumination light for the spectroscopic ellipsometry is coupled into the ATR prism 50 and through which the light is decoupled from the ATR prism 50 after interaction with the measured object. In this example, the coupling surface SBE is a plane surface. The ATR prism 50 has further a measuring surface (for example a plane surface) having a measuring portion M, which is in optical contact with the measured object. The measuring portion M may be arranged such as to contact a cutting surface of the cutting blade 53.

In the example shown in FIG. 1 the measured object is human tissue 72 freshly cut by the cutting blade 53 (i.e. cut immediately before the optical measurement) upon insertion of the measuring probe into the tissue 71 of a living organ (such as prostate, lung, breast, etc.). While cutting through the observed tissue 71, a thin fluid film is formed on the measuring portion M. The presence of the thin fluid film improves the optical contact between the measuring portion M and the observed tissue 72.

The ATR prism 50 has further a reflective surface (e.g. a plane surface) having a reflective portion RX constituted by a reflective layer 52 applied to the reflective surface. The reflective layer 52 may be for example a metal layer (such as an aluminum layer) or may exhibit a multilayer structure. Preferably the outermost layer of the multi-layer structure is a hard coating layer. The prism angle alpha_p between the reflective surface and the measuring surface (and more specifically between the measuring portion M and the reflective portion R) is selected such that the light undergoes an attenuated total reflection by the measuring portion and is reflected back to the measuring portion where it undergoes a second attenuated total reflection. Thus, the infrared light has twice an optical contact with the examined cut tissue 72: once prior and once after the reflection by the reflective portion RX. Preferably, the ATR prism 50 is configured such that prior and after the reflection by the reflective portion RX, the infrared light is incident on the substantially same part of the measuring surface (i.e. on the substantially same measuring portion or part of it). Thus, the infrared light is in optical contact with same portion of the examined tissue 72 both prior and after the reflection by the reflective surface. This contributes to enhancing the obtained measuring signal.

In order to miniaturize the ATR prism 50 and the measuring probe 10, it is preferable to slightly focus the incident light. Preferably, the diffraction-limited focal point is at or around the reflective portion RX of the reflective surface. In other words, the waist of the slightly focused light beam is at or around the reflective portion RX.

In every configuration of the ATR prism 50, the average value alpha_av of the magnitudes of the two angles of incidence on the measuring portion M of the measuring surface prior to and after the reflection by the reflective portion RX, respectively (alpha_av=(alpha_e1+alpha_e2)/2) is approximately equal to the prism angle alpha_p. For example, the critical total reflection angle is about 35° to 36° for an ATR prism of diamond (refractive index n=2.4 for the middle infrared spectral range), which is configured for measurements of human soft tissue with a reference index of about 1.4 in the middle infrared range. In this case the average value alpha_av is preferably around 41°. Preferably, the angle beta, which is the angle between the main ray of the light beam incident on the measuring surface M of the ATR prism 50 and the main ray of the exiting beam after the double total reflection at the measuring portion, is smaller than 12°. In the example shown in FIG. 1, the angle beta is about 2°. This may be achieved by configuring and arranging the ATR prism 50 such that the totally reflected light is incident on the reflective portion RX at an angle different from zero. In this case the angle beta is different from zero and may be configured to be smaller than 12°, preferably smaller than 10°, further preferably around 2°.

The relatively large difference between the average value alpha_av and the critical total reflection angle contributes to reducing the sensitivity of the ellipsometric arrangement with respect to angular deviations and not perfectly collimated incident light beams. In particular, due to the difference between the average value alpha_av and the critical total reflection angle, the random measuring error of the ellipsometric measurement may be significantly reduced.

For spectroscopic ellipsometric measurements, the measuring probe 10 with the ATR prism 50 is inserted into the observed organ up to a desired measurement point. The soft organ tissue 71 is cut by the cutting blade 53, whereby a portion of the freshly cut tissue comes in contact with the measuring surface M (with a thin fluid film being formed between the measuring portion M and the tissue 71). A spectroscopic ellipsometric measurement is carried out over the selected spectral ranges, each ellipsometric measurement comprising illuminating the measuring portion M with polarized light coupled into the ATR prism 50 through the coupling surface SBE, so that at least a portion of the light striking the measuring portion M undergoes an attenuated total reflection towards the reflective portion RX of the reflective surface and is back reflected by the reflecting portion towards the measuring portion M of the measuring surface, where it undergoes a second attenuated total reflection. After the second attenuated total reflection the polarized light is decoupled from the ATR prism 50 through the coupling surface SBE and directed in the detecting path comprising the analyzer 41 and the detector 30.

Based on the detected spectroscopic ellipsometric data, it is possible to determine—as known in the art—the ellipsometric parameters (for example Psi and phase difference Delta or a combination thereof) as a function of the wavelength (or wavenumber) in the selected spectral bands. Based on a comparison of the ellipsometric parameters or combinations thereof with known, reference ellipsometric parameters of various types of reference tissue samples (for example malign, tumor, healthy, etc. tissue samples) it is possible to detect cancer or to obtain information about the metabolism in the observed organ. In particular, certain characteristic features may be extracted from the measured ellipsometric spectra (for example by applying Principal Component Analysis (PCA) or other suitable statistical analysis method) and compared to reference characteristic features of the ellipsometric spectra. Preferably, the reference data is obtained on the basis of tissue samples from the same patient, said tissue sample having known properties (for example samples of surely healthy tissue and/or surely malign tissue identified as such by hystopathologic examination). The regions from which the reference tissue samples are obtained are preferably close to the observed (measured) regions.

Preferably, the measurement and data analysis are completed within short time, preferably within a few minutes. The results of the spectroscopic ellipsometric measurements may be presented to a surgeon and/or used in an automatic decision making process. The process of spectroscopic ellipsometric measurement as well as individual optical and/or mechanical elements may be, as known in the art, computer controlled, thereby automating the whole measurement process.

Figure 2:
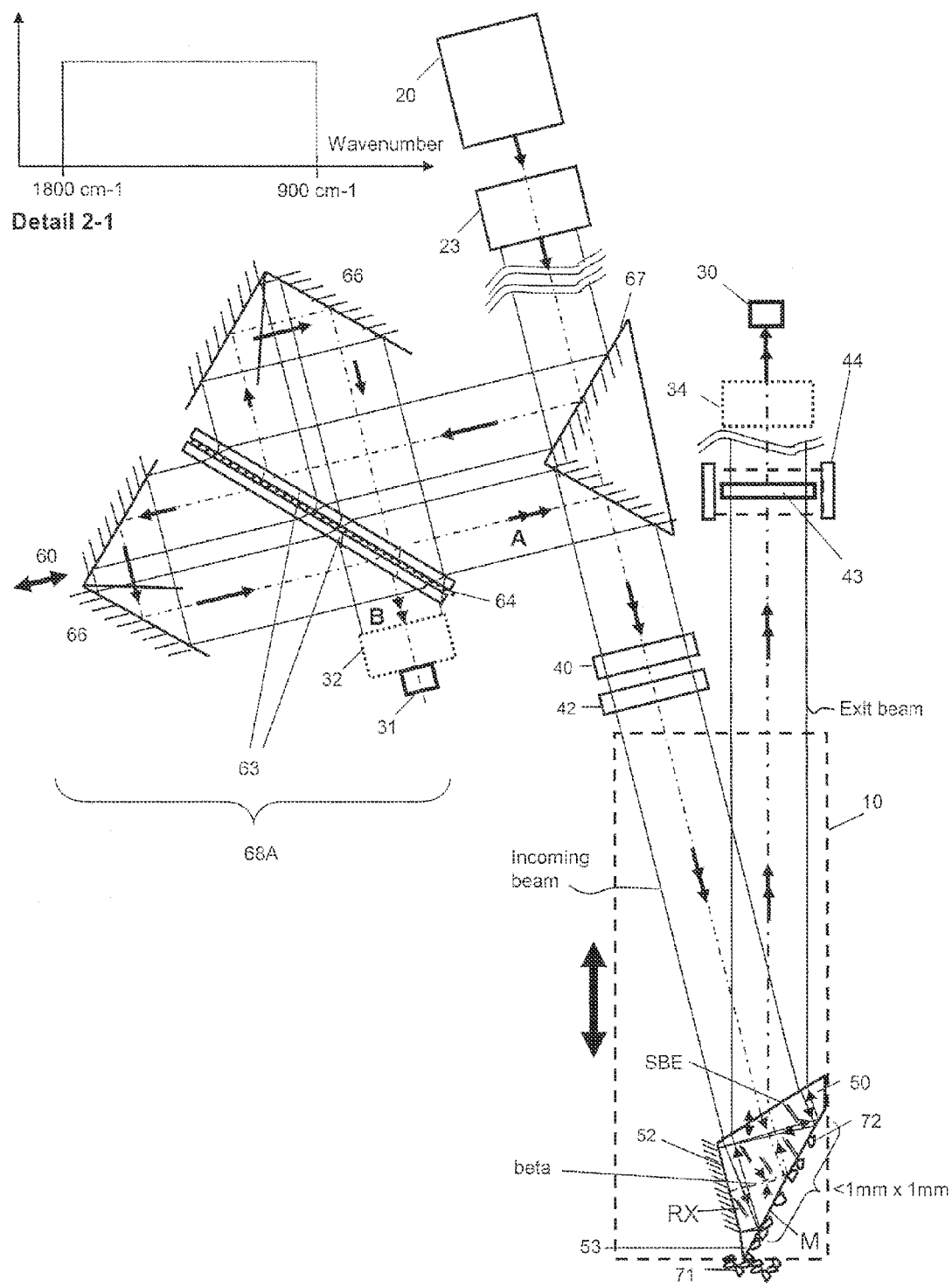

FIG. 2 shows schematically the optical layout of an apparatus for infrared spectroscopic ellipsometry for cancer and/or metabolism diagnosis according to a second example. The spectroscopic ellipsometer of this example is similar to the spectroscopic ellipsometer of the first example, with the following differences:

The spectroscopic ellipsometer shown in FIG. 2 is a Fourier spectroscopic ellipsometer. The Fourier spectroscopic ellipsometer comprises a broadband light source 20 emitting infrared light in the mid-infrared spectral range from 900 $cm^{-1}$ to 1800 $cm^{-1}$ (in wavenumbers). The broadband light source may be for example a quantum cascade laser battery emitting in infrared. The broadband light source emits light with a continuous or quasi-continuous spectrum, as shown in Detail 2-1. The emitted broadband light is coupled via suitable optical coupler 23 (for example fiber based optical coupler) with a collimator output into a beam expansion component. Preferably, the beam expansion component allows adjustment of cross-sectional beam size and/or characteristics.

The expanded light beam is coupled by means of a roof-edge type mirror 67 into an interferometer 68A comprising two triple-mirror type reflectors 66 (for example hollow cube type reflectors) and a beam splitter system comprising a beam splitter layer 64 sandwiched between two beam splitter plates 63. One of the triple-mirror type reflectors 66 is positioned on a computer controlled, motor driven translational or linear stage 60. This reflector 66 can be linearly translated along an axis, as indicated in FIG. 2 by the double-sided arrow. Thus, it is possible to introduce a variable and controllable path difference in the two arms of the interferometer 68A.

The above components enable to realize a Fourier spectrometer with a spectral resolution between 2 $cm^{-1}$ and 4 $cm^{-1}$. The further constituent elements of the Fourier spectrometer such as the reference path of the interferometer and the white light interference zero point setting element are not shown in FIG. 2.

The coupling of the interfering infrared light coming from the first output A of the interferometer 68A in the measuring probe 10 (via the polarizer 40 and the retarder 42) is realized by means of the roof-edge type mirror 67. At the second output B of the interferometer 68A a reference detector 31 with its corresponding optical system 32 is arranged. The detector 31 may be any suitable detector for infrared light, for example a mercury-cadmium-telluride (MCT) detector. The double output layout of the interferometer 68A enables the detection of the light source spectrum by means of Fourier transformation spectroscopy at one of the outputs. The determined spectrum may serve as a reference. As explained above, the interfering light emitted from the other output is used for spectroscopic ellipsometric measurements.

The remaining optical components, such as polarizer, analyzer, detector, measuring probe and ATR prism constituting the spectroscopic ellipsometric optical arrangement are the same or similar to those in the first example.

Figure 3:
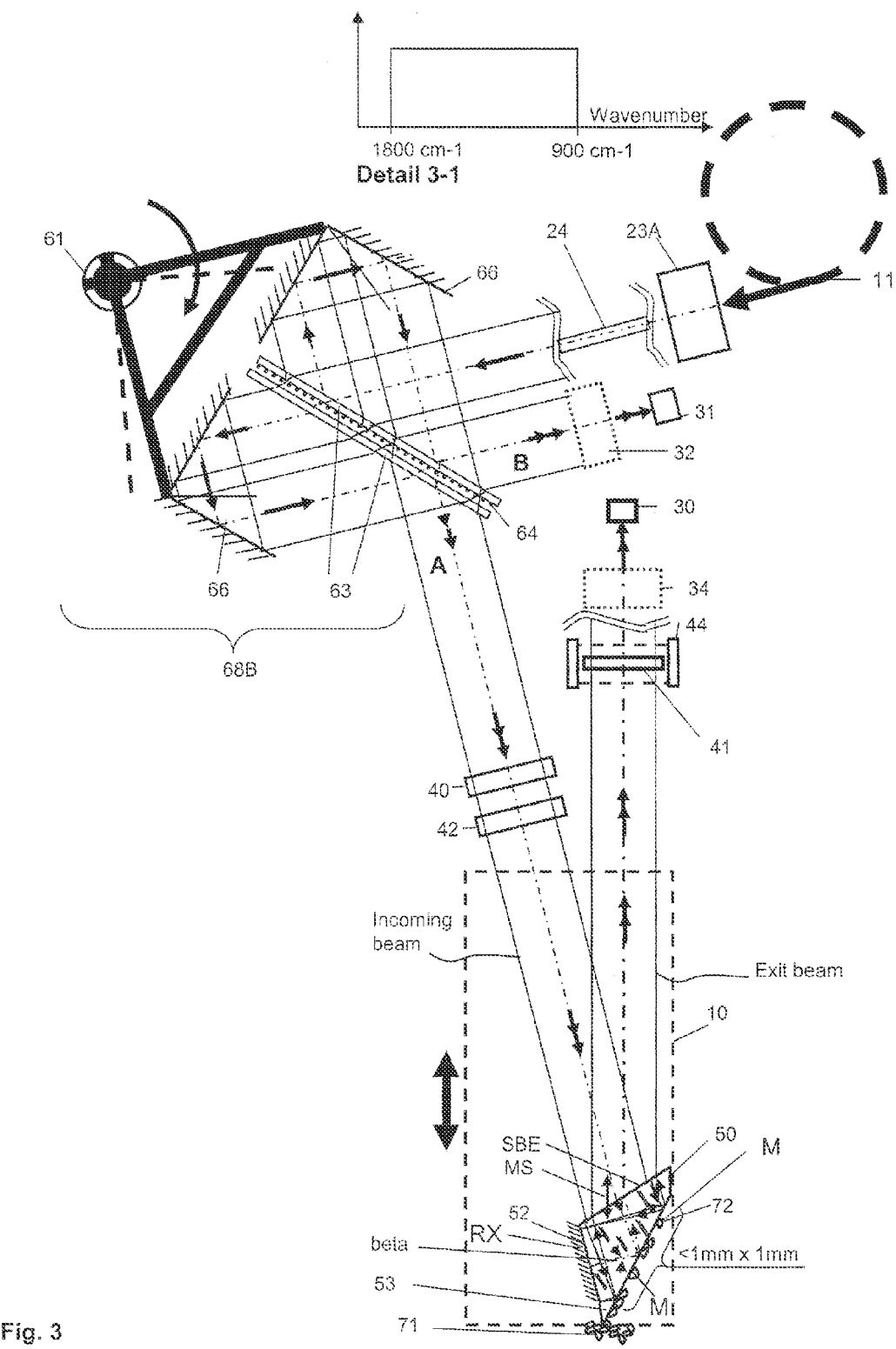

FIG. 3 shows schematically the optical layout of an apparatus for infrared spectroscopic ellipsometry for cancer and/or metabolism diagnosis according to a third example. The spectroscopic ellipsometer of this example is similar to spectroscopic ellipsometer of the first example, with the following differences:

The spectroscopic ellipsometer shown in FIG. 3 is a Fourier spectroscopic ellipsometer. The light source is the beamline of a synchrotron 11. For the purposes of spectroscopic ellipsometry, light in the mid-infrared range from 900 $cm^{-1}$ to 1800 $cm^{-1}$ is used. The continuous spectrum of the emitted light is shown in Detail 3-1. The emitted light is coupled by means of a fiber based optical coupler 23A to a silver halide fiber 24 and from there to a collimator (not shown in FIG. 3).

The collimated light beam enters an interferometer 68B comprising two triple-mirror type reflectors 66 and a beam splitter system comprising a beam splitter layer 64 sandwiched between two beam splitter plates 63. The interferometer 68B (which is a part of a Fourier transformation spectrometer with a spectral resolution between 2 cm$^{-1}$ and 4 cm$^{-1}$) comprises further a computer controlled drive system or actuator 61, e.g. a computer controlled rotational stage. The interferometric scan is realized by rotating the drive system or actuator 61, as shown in FIG. 3. An advantage of this type of rotating mirror type interferometer is that in its balanced state it is very robust with respect to vibrations due to environment influences.

As in the example shown in FIG. 3, the interferometer 68B has two outputs. One output (output B) may be used to detect the spectrum of the illumination light and use it as a reference spectrum. To this extent, the interfering light coming from the output B of the interferometer 68B may be detected by a suitable detector 31 (for example a mercury-cadmium telluride (MCT) detector) associated with a corresponding optical system 32 and subjected to a Fourier analysis (for example FFT algorithm).

The interference light coming from the other output (output A) of the interferometer 68A may be used for spectroscopic ellipsometric measurements by coupling it into a spectroscopic ellipsometric optical arrangement comprising a polarizer 40, a measuring probe 10 comprising an ATR prism 50, an analyzer 41 positioned on a rotary stage 44 and a detector 30 with a corresponding optical system 34. These elements are the same or similar to those in the first and the second example.

Figure 4:
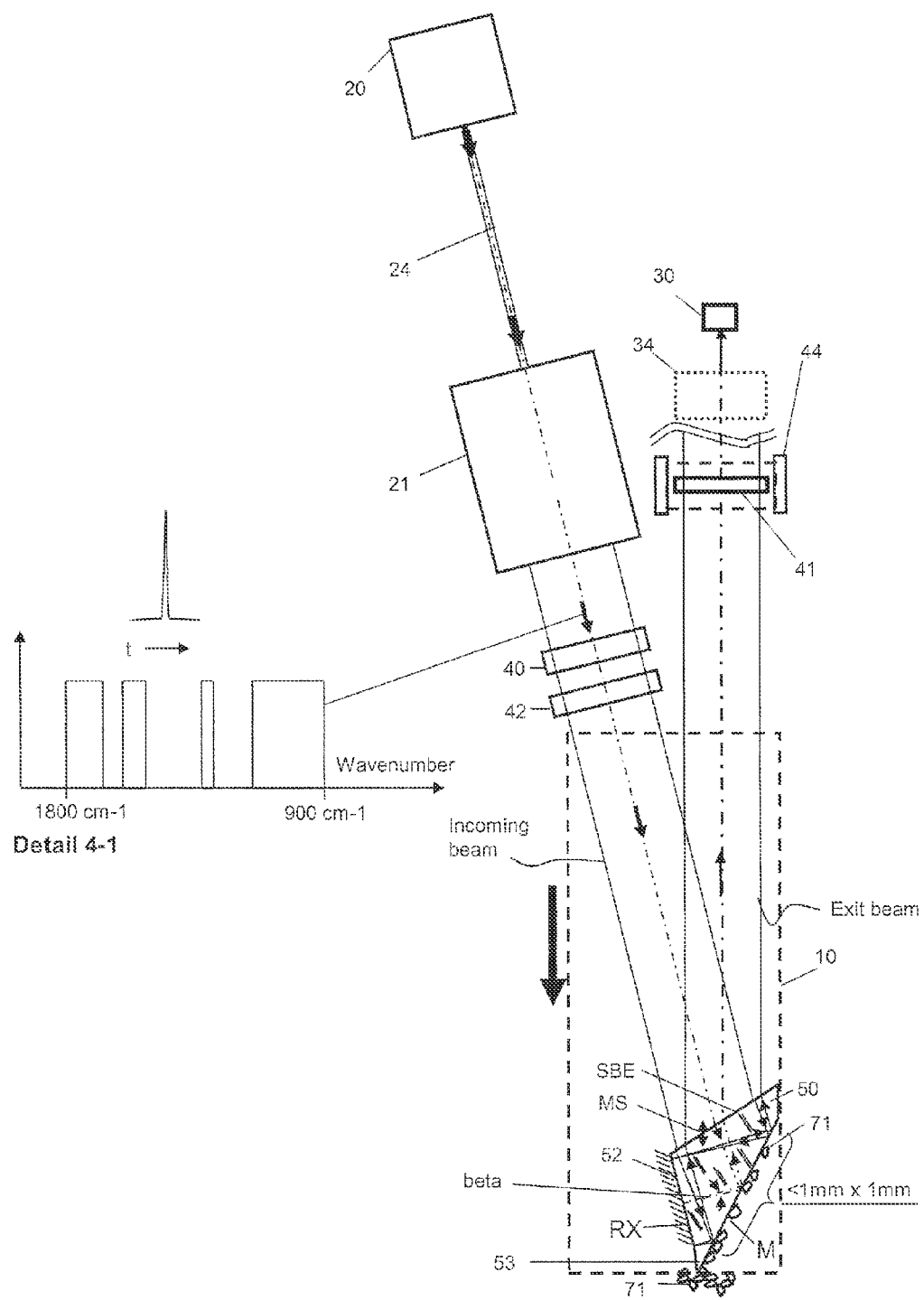

FIG. 4 shows schematically the optical layout of an apparatus for infrared spectroscopic ellipsometry for cancer and/or metabolism diagnosis according to a fourth example. The spectroscopic ellipsometer of this example is similar to the spectroscopic ellipsometer of the first example, with the following differences:

The light source is broadband light source 20 emitting infrared light with a substantially continuous spectrum (e.g. a broadband quantum cascade laser battery) 20. The spectroscopic ellipsometer comprises further a monochromator 21 (for example fiber coupled monochromator), operating in the spectral range from about 900 cm$^{-1}$ to 1800 cm$^{-1}$. The monochromator 21 preferably enables selection of individual spectral ranges (relevant for the cancer and/or metabolism diagnosis) as well as wavelength scanning in time as shown in Detail 4-1. The remaining optical elements are the same or similar to those of the first to third example.

Figure 5:
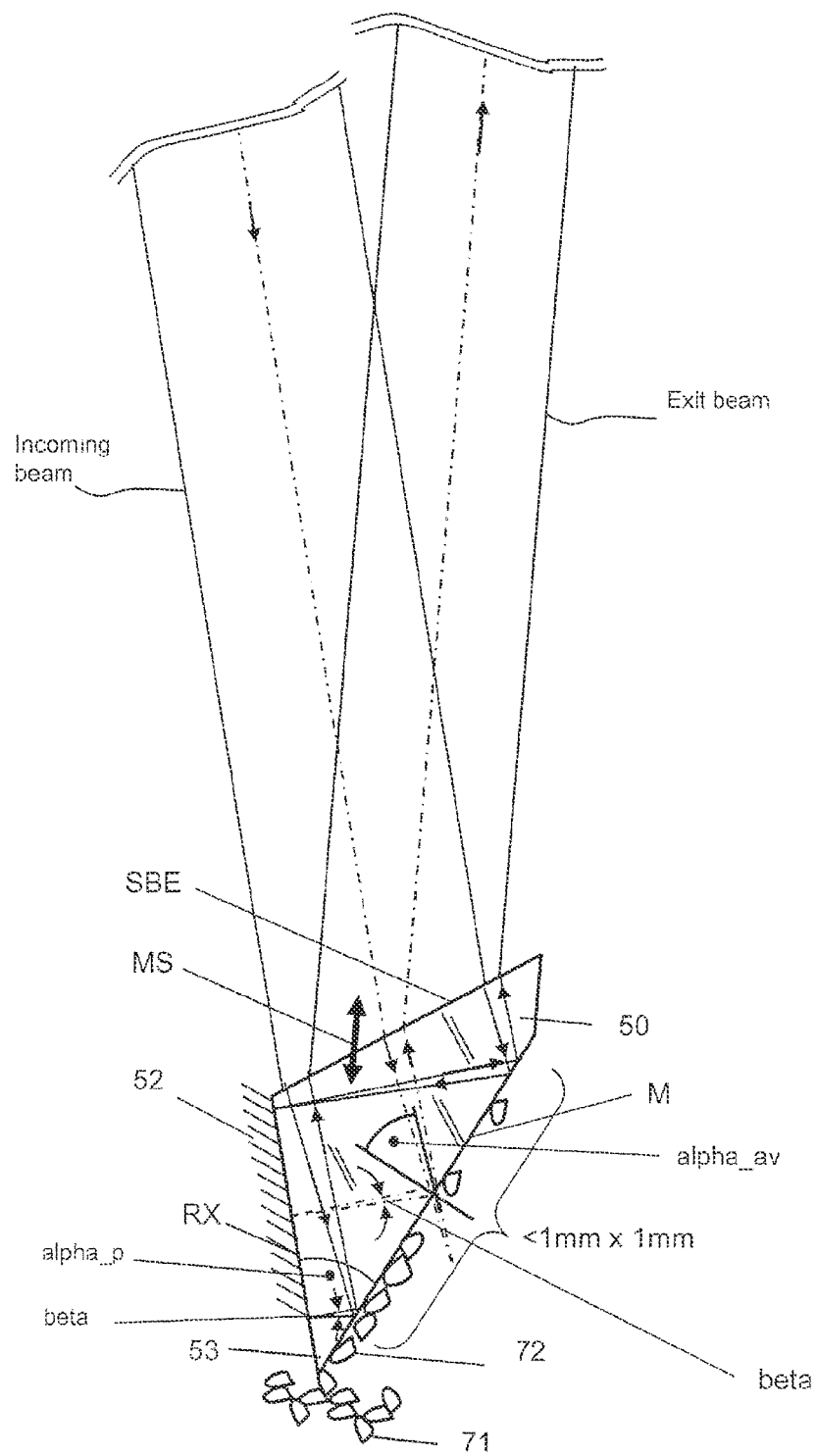
FIG. 5 shows an exemplary ATR prism.

FIG. 5 is a view of an exemplary ATR prism and shows the beam propagation through the prism. The ATR prism 50 is preferably made of diamond. The ATR prism 50 is similar to the prism employed in the apparatuses shown in FIGS. 1 to 4. As explained in connection with FIG. 1, an incoming light beam incident on the optical coupling surface SBE is refracted towards the measuring portion M of the measuring surface. The refracted beam strikes the measuring portion M at an angle around the critical total reflection angle and undergoes an attenuated total reflection. The totally reflected light reaches the reflective portion RX of the reflective surface and is reflected by the reflective layer 52 of the reflective portion RX towards the measuring portion M, where it undergoes a second attenuated total reflection. The attenuated totally reflected light exits through the optical coupling surface SBE, thereby forming an exit light beam. The double attenuated total reflection considerably enhances the measuring signal.

The ATR prism 50 exhibits a sharp tip or cutting edge 53 formed by the intersection of the measuring surface and the reflective surface. In other words in this example, the measuring surface and the reflective surface intersect to thereby form a sharp cutting blade 53 for cutting through the measured object. Alternatively, the cutting blade may be an additional element integrally formed with the ATR prism, as in the first to fourth examples. The ATR prism 50 may be subjected to micro vibrations MS, in order to assist the cutting process and reduce the collateral tissue damage.

As explained in connection with FIG. 1, the ATR prism 50 is configured such that the average value alpha_av (alpha_av= (alpha_e1+alpha_e2)/2) of the magnitudes of the two angles of incidence on the measuring surface prior to and after reflection by the reflective surface RX, respectively, is approximately equal to the angle alpha_p between the measuring portion M and the reflective portion RX. For example, for an ATR prism made of diamond, the average value alpha_av may be around 41°. Preferably, the angle beta, which is the angle between the main ray of the incoming light beam striking the measuring surface of the ATR prism 50 and the main ray of the light beam after double attenuated total reflection is smaller than 12°, for example about 2°.

Due to spectral dispersion and/or diffraction effects, there may exist a certain angular spread with an angle gamma at the exit of the ATR prism. The angular spread generally depends on the used spectral range. To compensate for the spectral dispersion, the ATR-prism 50 may comprise a blazed diffraction grating on the optical coupling surface SBE (not shown in FIG. 5). In an example, the blazed diffractive grating is configured to achromatize the optical system or to at least partially compensate for the angular spectral dispersion caused by the material of the ATR prism and any further optical elements.

For an ATR prism made of diamond configured to operate in mid-infrared the refractive index is about 2.4. The refractive index of the measured tissue is about 1.4 for this spectral range. Accordingly, the critical total reflection angle is about 35.7°. In this case, the angle of incidence of the main ray of the incoming light beam is preferably about 41°. At this angle there is an unrestricted attenuated total reflection at the measuring portion, even considering the spectral dispersion leading to an angular spread of the incoming light beam.

In the example shown in FIG. 5, the angle of light incidence on the reflective surface and more specifically on the reflective portion RX is different from zero. This results in an angular separation of the illumination light from the detection light (i.e. light that has undergone double attenuated total reflection) and facilitates the detection of reflected light.

Figure 6:
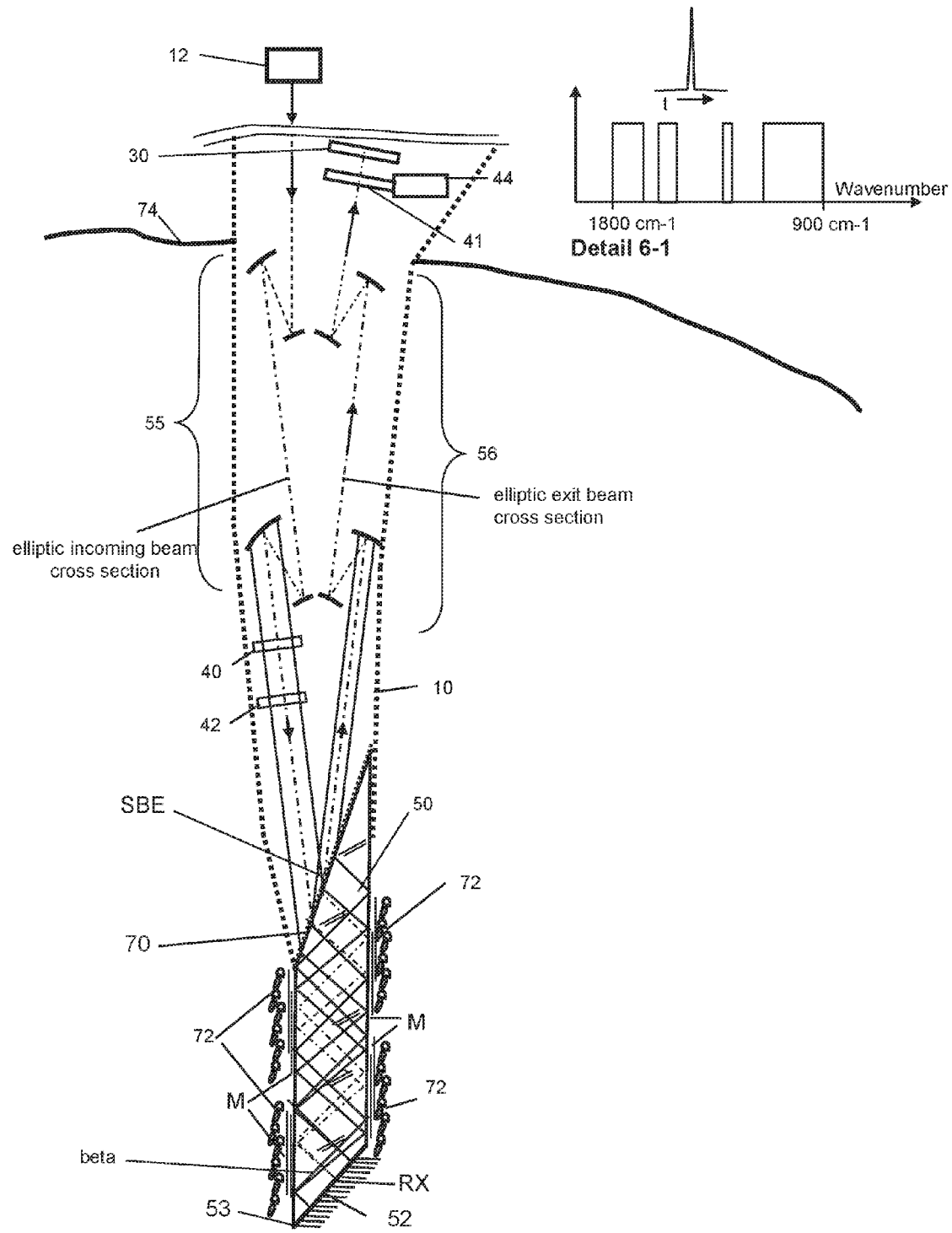
FIG. 6 shows an exemplary apparatus for infrared spectroscopic ellipsometry.

FIG. 6 shows schematically the optical layout of an apparatus for infrared spectroscopic ellipsometry for cancer and/or metabolism diagnosis according to a sixth example. This arrangement allows increasing the sensitivity of the spectroscopic ellipsometric measurements at the expense of the spatial resolution, since the measuring signals are collected from different spatial regions of the measured object.

The spectroscopic ellipsometer comprises a quantum cascade laser battery 12 with a variable wavelength as an infrared light source emitting light in the spectral range of 900 cm$^{-1}$ to 1800 cm$^{-1}$. Similar to the spectroscopic ellipsometer shown in FIG. 1, it is possible to select and optionally address (by for example amplitude or phase modulation) individual spectral bands known to provide information relevant for the spectroscopic ellipsometric measurements for cancer and/or metabolism diagnosis. Detail 6-1 shows the spectrum of the emitted infrared light with a number of selected spectral bands.

The optical arrangement comprises further a polarizer 40, a retarder (compensator) 42, an analyzer 41 positioned on a rotatory stage 44 and a detector 30 for detecting infrared light.

The components are substantially the same or similar to those described in connection with the previous examples.

The spectroscopic ellipsometer comprises an illumination path and a detection path. The illumination path comprises optical components 55 for adjusting the cross section of the incident light beam. Similarly, the detection path may comprise optical components 56 for adjusting the cross section of the exit light beam (i.e. the light beam exiting the ATR prism 50). The optical components 55 and the optical components 56 may each comprise a plurality of mirrors and/or lenses configured to form a beam with an elliptic cross section and to adjust the beam's cross section. At last a part of the optical components 55 and 56 may be integrated within the housing of the measuring probe 10.

The ATR prism 50 may be made of diamond and has two measuring surfaces and a substantially plane reflective surface intersecting the two measuring surfaces. The reflective surface has a reflecting layer 52 forming a reflective portion RX. The reflective surface is formed at the tip of the measuring probe and connects the two measuring surfaces. A cutting blade 53 is formed by the intersection of one of the measuring surfaces and the reflective surface. It is, however, possible to form a cutting blade as a separate element integral with the remaining parts of the ATR prism 50.

Each of the two measuring surfaces comprises a plurality of measuring portions M that are in optical contact with the measured object, where attenuated total reflection occurs. In particular, the ATR prism 50 is configured such that the incoming light entering the ATR prism 50 through the optical coupling surface SBE undergoes multiple attenuated total reflections at each measuring surface while propagating between the measuring surfaces (similar to the light propagation in an optical fiber). In the example shown in FIG. 6, the incident light undergoes two attenuated total reflections at the right and two attenuated total reflection at the left measuring surface and is subsequently reflected by the reflecting portion RX, thereby undergoing again multiple attenuated total reflections at each of the measuring surfaces while propagating back through the ATR prism 50 towards the optical coupling surface SBE. At each attenuated total reflection, the light contacts different measuring portions of the measuring surfaces and thus different regions of the measured object 72 (for example freshly cut human tissue). This leads to enhancement of the measuring signal. However, the spatial resolution of the measurement is decreased.

In order to compensate for the spectral dispersion causing angular spread, a blazed diffractive grating 70 may be formed on the optical coupling surface SBE.

Figure 7:
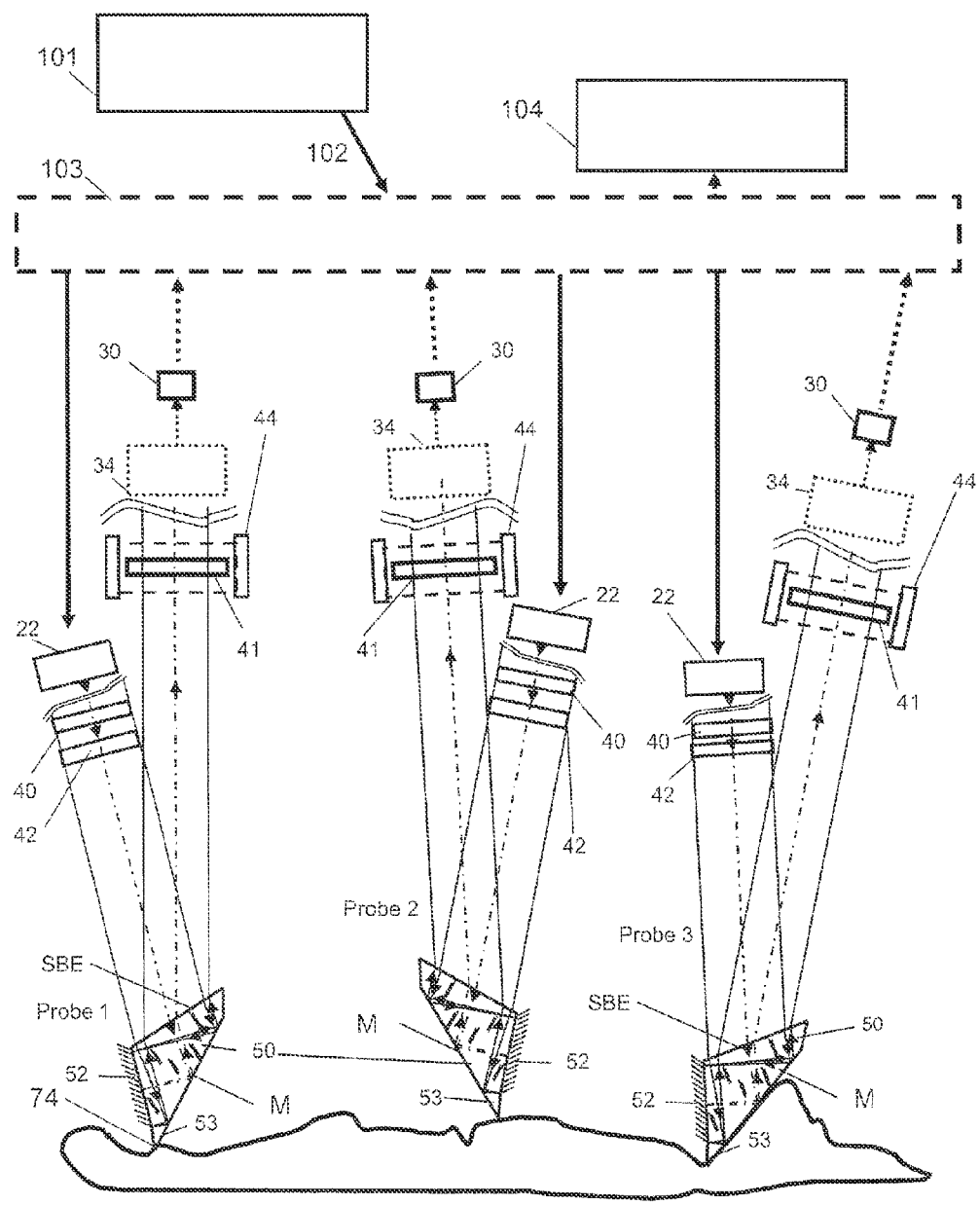
FIG. 7 shows an exemplary apparatus for infrared spectroscopic ellipsometry using a kit of measuring probes.

FIG. 7 shows an apparatus for infrared spectroscopic ellipsometry for in-vivo cancer diagnostics operating in the mid-infrared range of about 900 cm$^{-1}$ to 1800 cm$^{-1}$. The spectroscopic ellipsometer (which may be any of the spectroscopic ellipsometers described in the present application) comprises a kit or a magazine that includes a plurality of measuring probes with the associated optical systems. In FIG. 7 only three measuring probes (Probe 1 to Probe 3) are shown. The number of measuring probes may vary, for example a kit or a magazine containing up to 36 measuring probes may be provided.

The measuring probes may be of the same type or may differ. In particular, each measuring probe may have an ATR prism with different angle between the measuring and reflective surface.

It is possible to carry out multiple measurements in parallel by employing a plurality of measuring probes (for example of the same type) positioned at different spatial positions of the measured object (e.g. a human organ). Each measurement and respective data analysis is preferably carried out within a couple of minutes and the overall measurement and analysis time preferably does not exceed 20 minutes. Thus for example, it is possible to obtain information about the spatial distribution of cancer or other malign tissue in an affected organ during a surgical intervention and use this information to support the decision of the surgeon, whether to incise a particular portion of the organ or not.

Although in FIG. 7 each of the measuring probes is shown as being associated with a separate illumination and detection path, the individual probes may share at least a portion of their illumination and/or detection paths.

Alternatively, the measurements may be carried out serially, by selecting a different probe for each measurement. For example, it is possible to repeat the measurements using measuring probes specifically configured for measurements on different materials. Further, a contaminated measuring probe may be exchanged for a new one. Due to the invariance of the average value alpha_av, the alignment of the optical system after change of the measuring probe is relatively simple and may be carried out automatically.

The spectroscopic ellipsometer shown in FIG. 7 may advantageously employ a multi-channel spectrometer, in particular a multi-channel Fourier spectrometer, such as for example disclosed in DE 10 2012 023 248. Every channel of this rotating tower interferometer may be optically coupled to a different measuring probe of the kit of measuring probes. The measuring probes may be arranged such that they are easily accessible to the surgeon under surgery conditions.

Figure 8:
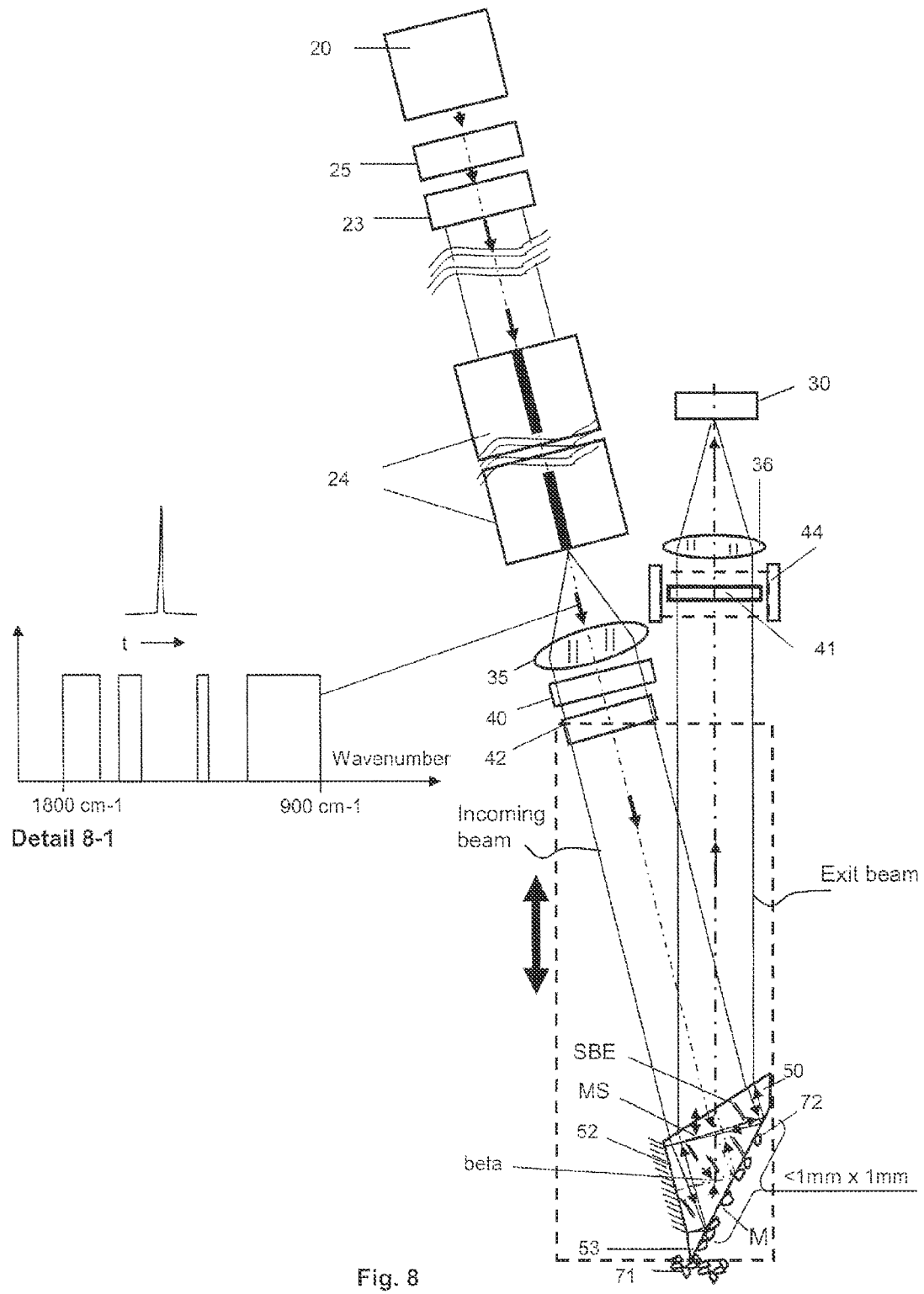
FIG. 8 shows an exemplary apparatus for infrared spectroscopic ellipsometry.

FIG. 8 shows schematically the optical layout of an apparatus for infrared spectroscopic ellipsometry for cancer and/or metabolism diagnosis according to a seventh example. The spectroscopic ellipsometer according to this example is similar to the spectroscopic ellipsometer according to the first example, with the following differences:

The illumination path comprises a fiber coupled hyper-spectral modulator 25, such as for example the one disclosed in DE 10 2014 002 514. The hyper-spectral modulator 25 is positioned after the broadband infrared light source 20 (for example a quantum cascade laser battery emitting infrared light in the spectral range of 900 cm$^{-1}$ to 1800 cm$^{-1}$) and upstream of a fiber based optical coupling system 23 comprising a collimator. The hyper-spectral modulator 25 enables a serial wavelength scan of the broadband spectral range (e.g. the broadband mid-infrared range). Further, the hyper-spectral modulator 25 preferably allows a selection of specific spectral bands for the spectroscopic ellipsometric measurements. The spectrum of the illumination light showing the selected spectral bands is shown in Detail 8-1.

The light beam is coupled to a silver-halide optical fiber 24 and directed towards a collimator lens 35 that expands the light beam. The remaining optical components, such as a polarizer 40, an analyzer 41, a detector 30, a measuring probe 10 and ATR prism 50 constituting the spectroscopic ellipsometric optical arrangement are generally the same or similar to those of the previous examples.

FIG. 9 shows schematically the optical layout of an apparatus for infrared spectroscopic ellipsometry for cancer and/or metabolism diagnosis according to an eight example. The illumination path of the spectroscopic ellipsometer of this example includes a broadband infrared light source 12 (such as for example a quantum cascade laser battery) with a variable (scannable) wavelength (having optionally an integrated collimator), a polarizer 40 and a retarder 42. The collimated light beam is coupled to a measuring probe 10 having a slightly conical shape with an ATR prism 50 arranged at its tip. The ATR prism 50, which is shown in more detail in Detail 9-1, is generally the same as the one described in connection with the previous figures. In FIG. 9, the ATR prism 50 is shown as being substantially outside of the hosing of the measuring probe. However, it is possible to arrange the ATR prism 50 such that it is at least partially enclosed within the hosing of the measuring probe 10. Detail 9-2 shows the spectrum of the light source 12. Due to dispersion, there may be an angular spread (not shown) at the exit of the ATR prism (for example an ATR prism made of diamond).

The remaining optical components, such as a polarizer 40, an analyzer 41, a detector 30, a measuring probe 10 and ATR prism 50 constituting the spectroscopic ellipsometric optical arrangement are generally the same or similar to those of the previous examples.

FIG. 10 shows schematically the optical layout of an apparatus for infrared spectroscopic ellipsometry for cancer and/or metabolism diagnosis according to a ninth example. The spectroscopic ellipsometer according to this example is similar to the spectroscopic ellipsometer according to the eight example, with the difference that the measuring probe comprises an elongated beam guide element that has a reflective coating 69 in at least a portion thereof. Detail 10-1 is an enlarged view of the ATR prism 50. The measuring part M of the ATR prism may have a size equal to or smaller than 0.5 mm×0.5 mm.

Figure 11A:
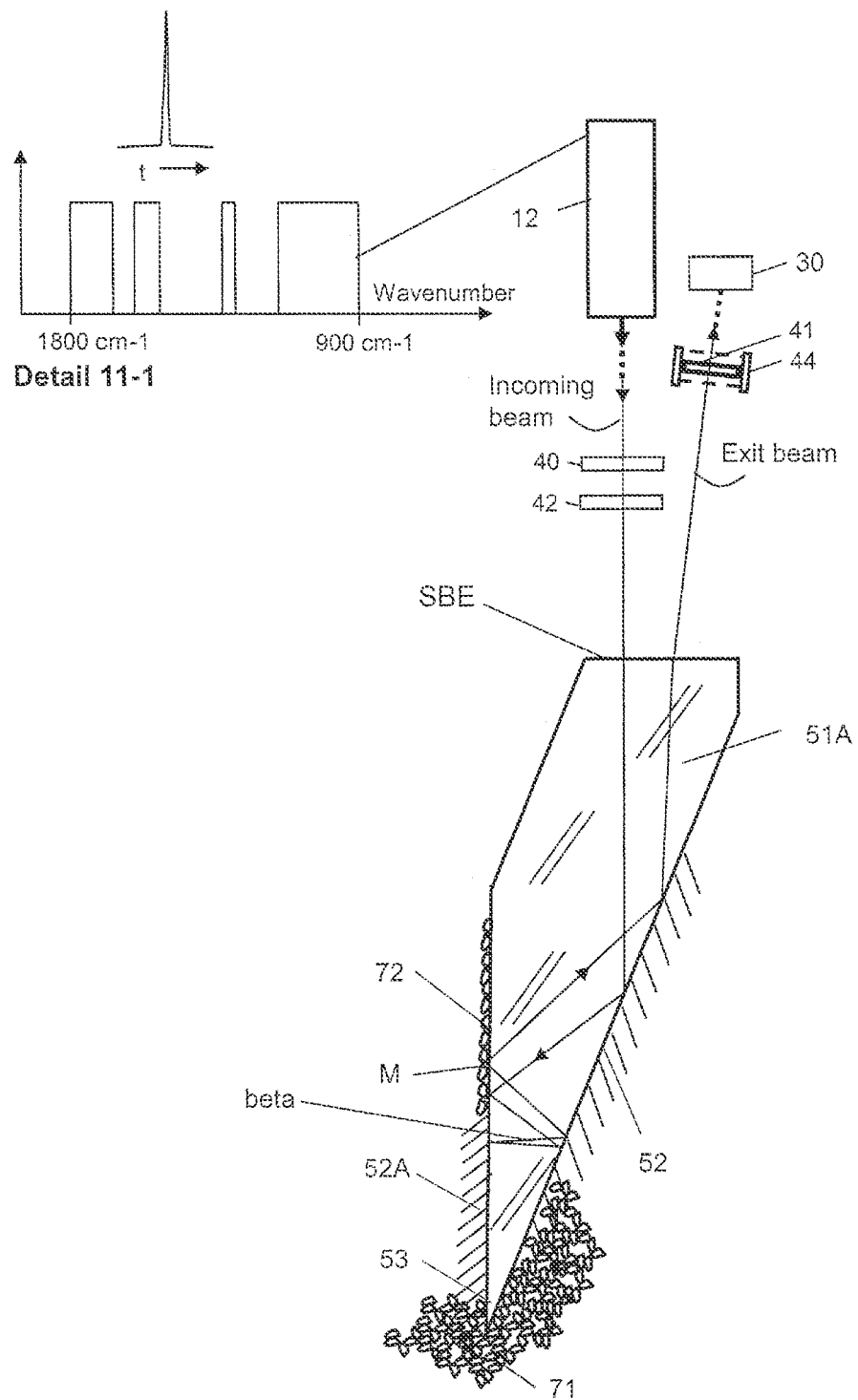
FIG. 11A shows an exemplary apparatus for infrared spectroscopic ellipsometry.

FIG. 11A shows schematically the optical layout of an apparatus for infrared spectroscopic ellipsometry for cancer and/or metabolism diagnosis according to a tenth example. The ATR prism 51 employed in this example is fabricated as a relatively thin synthetic diamond plate, for example a diamond plate having a thickness of about 1.8 mm. The ATR prism has an optical coupling surface SBE, which is a substantially plane surface, and two surfaces, which intersect with each other, thereby forming a cutting blade 53 with a cutting angle of approximately 20° (alpha_p=20°). Due to the sharp cutting blade 53 with small cutting angle, it is possible to easily insert the measuring probe 10 into the measured object and cut through the tissue 71 (for example a human organ).

One of the intersecting surfaces (measuring surface) comprises a measuring portion M configured to be brought into optical contact with the measured object 72. The measuring surface comprises furthermore a reflective portion formed by applying a reflective layer 52A on part of the measuring surface. The other one of the intersecting surfaces (reflective surface) comprises a reflective portion RX formed by a reflective layer 52. The ATR prism 51A is configured such that light incident on measuring portion M of the measuring surface undergoes a first attenuated total reflection and is guided back to the measuring portion M for a second attenuated total reflection by means of a reflection by the reflective layer 52, a reflection by the reflective layer 52A covering the reflective portion of the measuring surface and a second reflection by the reflective layer 52. Having undergone a second attenuated total reflection, the light is guided through to the optical coupling surface SBE by means of a reflection at the reflective surface.

The remaining components, such as polarizer 40, analyzer 41, retarder 42, rotary stage 44, detector 30, etc. constituting the optical spectroscopic ellipsometric arrangement are the same as in the first example. Not shown in FIG. 11A is the housing (for example a stainless steel housing) of the measuring probe.

Figure 11B:
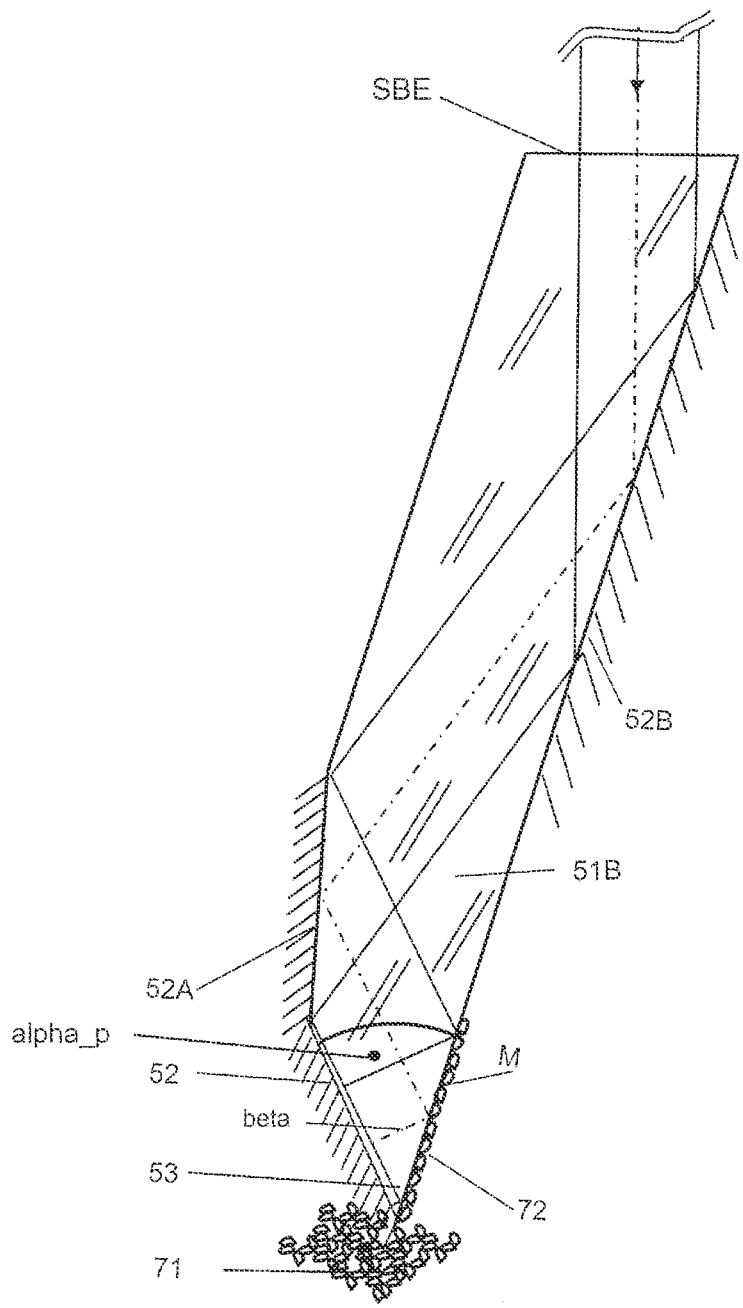
FIGS. 11B to 11D show exemplary ATR prisms that may be used for example in the apparatus shown in FIG. 11A.

FIG. 11B shows another ATR prism 51B that may be used in any of the described spectroscopic ellipsometers, for example in the one shown in FIG. 11A. The ATR prism 51B is made of diamond and has two reflective surfaces, the first reflective surface being formed by the reflective layer 52 and the second reflective surface by the reflective layer 52A. The two reflective surfaces are formed at angle to each other. The measuring surface comprises a measuring portion M configured to be brought into contact with the measured object 72, where attenuated total reflection occurs. The measuring surface comprises further a reflective portion formed by the reflective layer 52B covering a part of the measuring surface. The measuring surface intersects with the first reflective surface, thereby forming a cutting blade 53 for cutting through the observed tissue 71.

The light passing through the optical coupling surface SBE is guided to the measuring portion of the measuring surface M by means of reflection at the reflective layer 52B of the measuring surface and a reflection at the first reflective surface or the second reflective surface. There the incident light undergoes a first total reflection. The totally reflected light is guided back to the measuring portion for a second attenuated total reflection by means of a reflection by the first reflective surface. Having undergone a second attenuated total reflection, the light is guided to the optical coupling surface SBE by means of a reflection at the reflective layer 52B of the measuring surface M and for some rays also at the second reflective surface. In the configuration shown in FIG. 11B the optical paths of the incident light beam entering the ATR prism 52B and the light beam leaving the ATR prism 52B are substantially the same. Since the angle of incidence (for both the incoming and the exiting light) at the optical coupling surface is substantially zero or close to zero, the angular dispersion at the exit of the ATR prism is very low. The separation of the incoming and the exit light beam may be achieved by suitable optical means, for example a beam splitter.

It is, however, possible to configure the ATR prism 52B such that the angle of incidence of the main ray of the incoming light beam on the optical coupling surface SBE is different than zero, so that the incoming light mean may be more easily separated from the exit light beam.

Figure 11C:
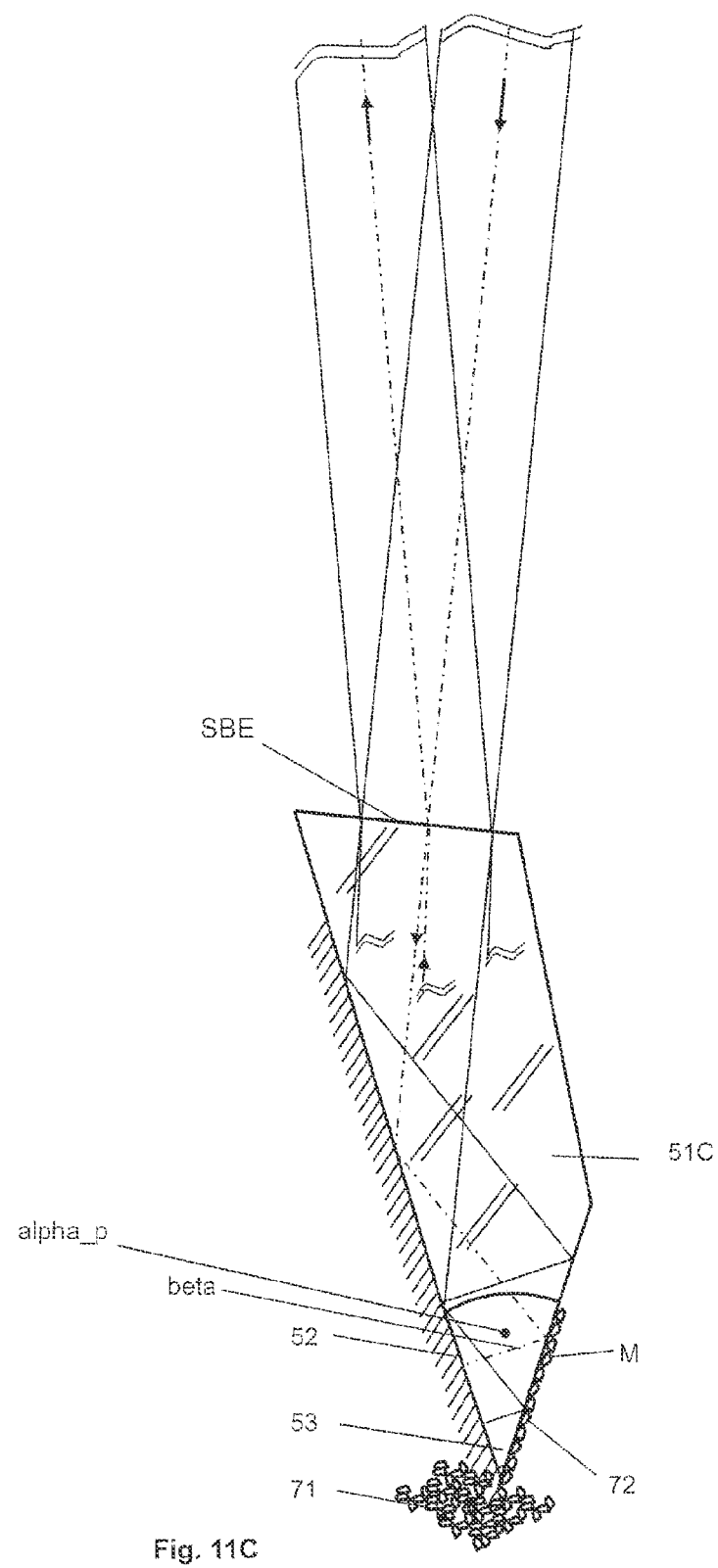

FIG. 11C shows another ATR prism 51C that may be used in any of the described spectroscopic ellipsometers, for example in the one shown in FIG. 11A. The ATR prism 51C comprises a measuring surface and a reflective surface having a reflective portion formed by applying a reflective layer 52 on the reflective surface. The measuring surface and the reflective surface intersect to form a cutting blade 53 with a cutting angle, which is equal to the prism angle. In the example shown in FIG. 11C the prism angle is about 39°-40°. The angle beta is about 2°. The ATR prism exhibits relatively low angular dispersion at its output.

Figure 11D:
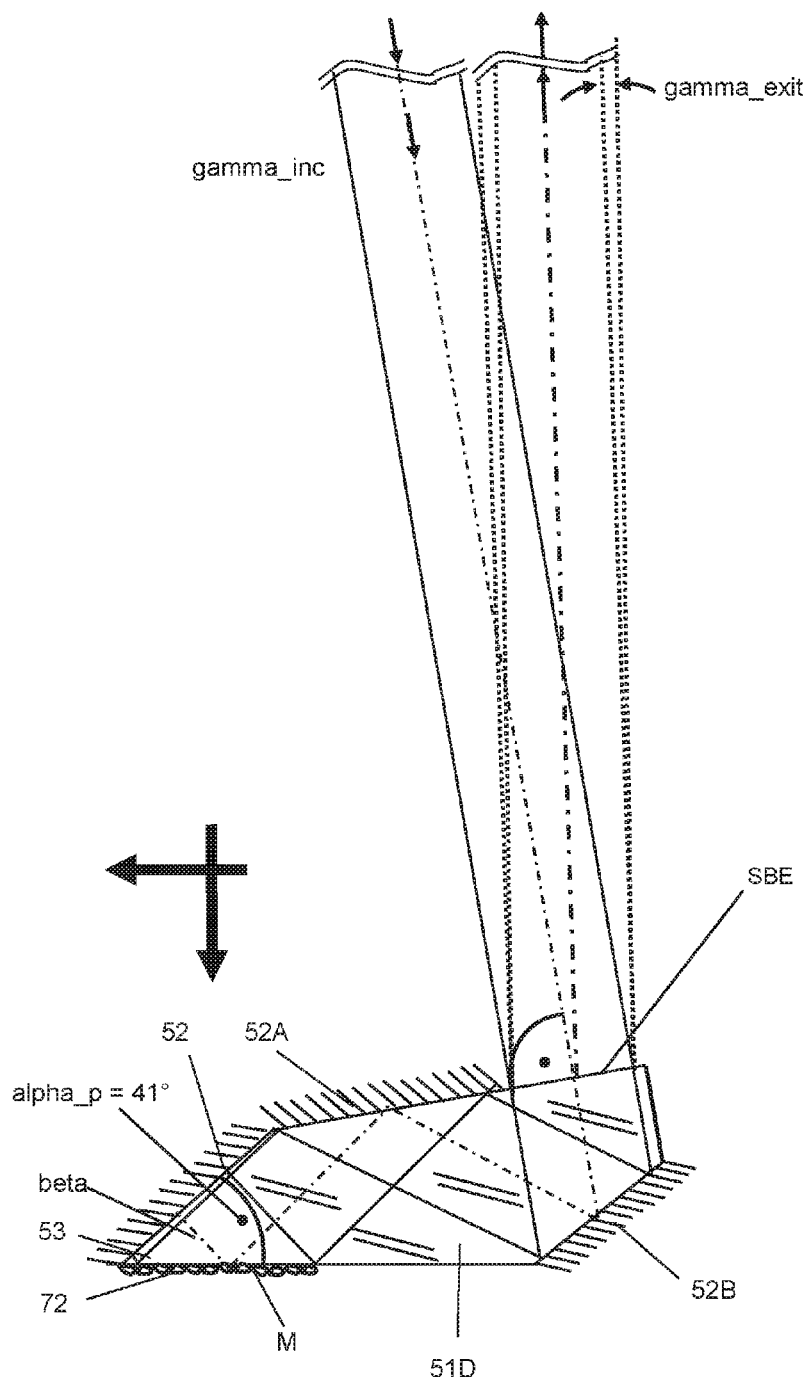

FIG. 11D shows another ATR prism 51D that may be used in any of the spectroscopic ellipsometers. The ATR prism 51D is arranged in the measuring probe in a substantially horizontal direction and is configured to the placed on the measured object, rather than inserted in it. The ATR prism 51D comprises a measuring surface with a measuring portion M configured to be brought into contact with the observed object 72 (for example human tissue). The ATR prism 51D comprises further two reflective surfaces arranged at an angle to each other and a third reflective surface. In the example shown in FIG. 11D the two angled reflective surfaces are fully covered by reflective layers 52A and 52, respectively. The third reflective surface is fully covered by a reflective layer 52B. However, the respective reflective surfaces may also be partially covered by reflective layers.

On one side, the measuring surface intersects with a first one of the angled reflective surfaces (i.e. the surface having reflective layer 52). On its other side it intersects with the third reflective surface (i.e. the surface having reflective layer 52B). The reflective surfaces and the measuring surface are arranged such that the light undergoes a double total reflection at the measuring portion M of the measuring surface and is guided in- and out of the ATR-prism, respectively. The prism angle alpha_p, which is the angle between the measuring surface and the reflective surface with the reflective layer 52 is in this example about 41° and the angle beta about 2°. Generally, the angle beta is preferably smaller than 12°. The incoming light beam is incident normally on the optical coupling surface SBE, so that the angular spread of the incoming light beam due to dispersion is approximately zero (i.e. gamma_inc≈0°). The exit light beam exhibits an angular spread gamma exit due to dispersion that is different from zero. Preferably, the detection path is configured such that even the outermost rays of the exit light beam are still detected by the detector.

The ATR prism 51D shown in FIG. 11D comprises a cutting blade 53. However, the ATR prism need not comprise a cutting blade if it is used only for measurements in horizontal position, while being placed on the measured object.

Figure 12:
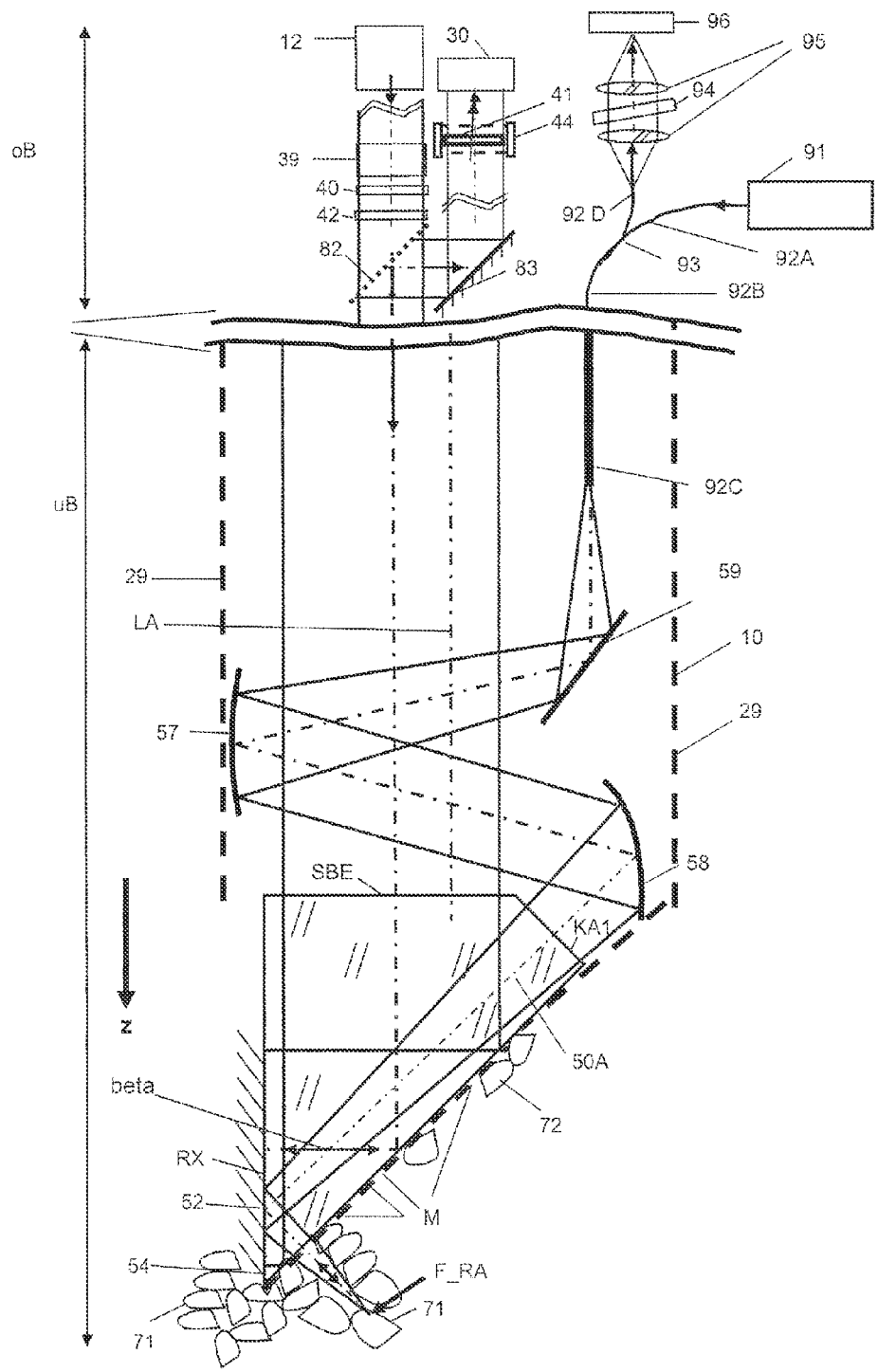
FIG. 12 shows an exemplary apparatus for infrared spectroscopic ellipsometry.

FIG. 12 shows an exemplary apparatus for spectroscopic ellipsometry with an integrated Raman spectroscopy optical arrangement. The spectroscopic ellipsometer may be any of the described spectroscopic ellipsometers. The optical arrangement is not shown up to scale, in particular the lower part uB is shown enlarged and the upper part oU downsized.

In addition to spectroscopic ellipsometry illumination and detection paths, the spectroscopic ellipsometer comprises a Raman spectroscopy illumination path and a Raman spectroscopy detection path. The Raman spectroscopy illumination path comprises a Raman excitation laser 91 (for example Nd:Yag-Laser emitting Raman excitation light with a wavelength of 1064 nm), a Y fiber coupler 93 that couples a monomode fiber 92A of the illumination path and a monomode fiber of the detection path 92D to a monomode fiber 92B outside the measuring probe, a monomode fiber 92C inside the housing 29 of the measuring probe, a mirror 59 (beam diverting mirror), a first off-axis parabolic mirror 57 and a second off-axis parabolic mirror 58. The mirror 59, the first off-axis parabolic mirror 57, the second off-axis parabolic mirror 58, the monomode fibers 92B and 92C and the Y coupler 93 are also part of the Raman spectroscopy detection path which further comprises an optical transfer system 95 (comprising for example two lenses), a notch filter 94 and a Fourier spectrometer for spectrally analyzing the scattered Raman light 96. In an example, the notch-filter blocks the Raman excitation light with wavelength 1064 nm emitted from the laser 91.

The monomode fiber 92B confocally discriminates the light returned from the measured object and thus eliminates the portion of the (non-Raman) scattered light during Raman spectroscopy measurement.

The first off-axis parabolic mirror 57 and/or the second off-axis parabolic mirror 58 may be configured to correct or at least partially compensate the overall aberrations in the optical path. In an example, the mirrors 50 and/or 59 may include an aberration corrective function to correct or at least partially compensate for the overall aberrations in the optical path. The mirror 59, the first off-axis parabolic mirror 57, the second off-axis parabolic mirror 58 and optionally any further optical elements may be integrated within the housing 29 (for example a stainless steel housing) of the measuring probe.

The ATR prism 50A (for example a diamond ATR prism) is used as an optical coupling element for both spectroscopic ellipsometry and Raman spectroscopy measurements. To couple the Raman excitation light into the ATR prism 50A and decouple the scattered Raman light returned from the measured object, the ATR prism exhibits a second optical coupling surface KA1. The second coupling surface may be a plane surface or a curved surface (for example a convex or concave surface). The measuring surface M of the ATR prism 50A serves as a surface for coupling both the attenuated totally reflected light for spectroscopic ellipsometry measurement and Raman excitation light into the measured object 72.

The Raman excitation light is focused at point F_RA. The scattered Raman light returned from the measured object enters through the measuring surface into the ATR prism 50A. The ATR prism 50A comprises further a reflective surface having a reflective portion formed by a reflective layer 52, which directs the totally reflected light back to the measuring portion M, where it undergoes a second attenuated total reflection. It is thus possible to carry out substantially simultaneously and at substantially the same measuring site both spectroscopic ellipsometric measurements and Raman spectroscopy measurements.

In the example shown in FIG. 12, the incoming light for spectroscopic ellipsometric measurement is incident on the optical coupling surface SBE of the ATR prism 50A substantially normally. Further, the ATR prism 50A is configured such that the angle beta is approximately zero. The incoming light is separated from the exiting light for spectroscopic ellipsometric measurement by means of a beam splitter 82 and a mirror 83.

Instead of providing a spectroscopic ellipsometer having two separate measuring paths (one for the spectroscopic ellipsometry measurements and one for the Raman spectroscopy measurements) it is possible to use a single two-channel Fourier spectrometer, the first channel being used for detection and analysis of the Raman scattered light (such as NIR Raman scattered light) and the second channel being used for spectroscopic ellipsometric measurements. It is also possible to employ a broadband one-channel Fourier spectrometer with $CAF_2$-components for both NIR Raman scattered light analysis and for spectroscopic ellipsometric analysis up to a wavenumber of about 1100 $cm^{-1}$, in combination with an infrared broadband laser and integration of the Raman spectroscopy measuring path and the spectroscopic ellipsometry measuring path.

Further, instead of having a Raman spectroscopy measuring path, the spectroscopic ellipsometer may have an optical coherence tomography measuring path, a microscopic measuring path, etc. Thus, the second optical coupling surface KA1 of the ATR prism may be configured for coupling optical coherence tomography light (in particular swept-source spectral-domain OCT), microscopic light in the visible region, etc.

The spectroscopic ellipsometer may integrate a plurality of further optical sensors or optical image forming or measuring systems, such as for example the above mentioned Raman spectroscopy sensors, OCT sensors (in particular swept source OCT sensors), microscopic observation, etc. The Raman spectroscopy sensors and the OCT sensors may operate in the near infrared spectral range and the microscopic observation may be carried out in visible range. The ATR prism may be dimensioned accordingly and comprise further optical coupling surfaces. All sensors may use the same measuring surface of the ATR prism (which is in optical and preferably mechanical contact with the measured object) to couple the respective measurement light into the measured object.

Figure 13:
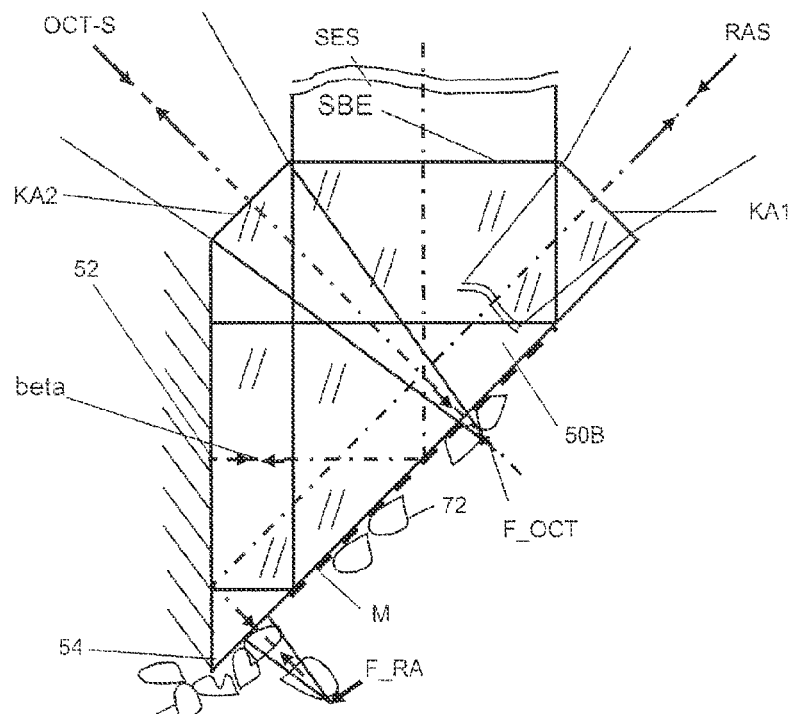
FIGS. 13 to 16 show exemplary ATR prisms for combining spectroscopic ellipsometric measurements with additional optical measurements.

FIG. 13 shows an exemplary ATR prism 50B (for example a diamond ATR prism) which is configured to serve as an optical coupling element for spectroscopic ellipsometry, Raman spectroscopy measurements and optical coherence tomography measurements.

The ATR prism 50B has a first optical coupling surface SBE for coupling and decoupling a polarized light for the spectroscopic ellipsometry, a second optical coupling surface KA1 for coupling and decoupling light for the Raman spectroscopy and a third optical coupling surface KA2 for coupling and decoupling light for the optical coherence tomography measurements. The first coupling surface SBE, the second coupling surface KA1 and the third coupling surface KA2 are substantially plane surfaces.

The measuring surface serves as a surface for coupling all three light beams (i.e. the totally reflected evanescent light beam, the Raman excitation light beam and the optical coherence tomography light beam) into the measured object 72. The Raman excitation light is focused at point F_RA and the optical coherence tomography light at point F_OCT. The dashed line on the measuring surface indicates the measuring portion M used for the attenuated total reflection (i.e. for the spectrometric ellipsometric measurement). The beam path of spectroscopic ellipsometry is indicated as SES, the beam path of the Raman spectroscopy as RAS and the beam path of the optical coherence tomography as OCT-S The ATR prism 50B comprises further a reflective surface RX having a reflective portion formed by a reflective layer 52, which directs the light undergone a first attenuated total reflection back to the measuring portion M, where it undergoes a second attenuated total reflection.

With the ATR prism 50B shown in FIG. 13 it is possible to carry out substantially simultaneously and at substantially the same measuring site of the measured object 72 spectroscopic ellipsometric measurements, Raman spectroscopy measurements and OCT measurements.

In the above example, it is possible to couple near infrared light for microscopic observation in the near infrared spectral range via the second optical coupling surface KA1 or the third optical coupling surface KA3. The microscopic measurement path may be at least approximately parallel to the OCT measurement path or the Raman spectroscopy measurement path.

Figure 14:
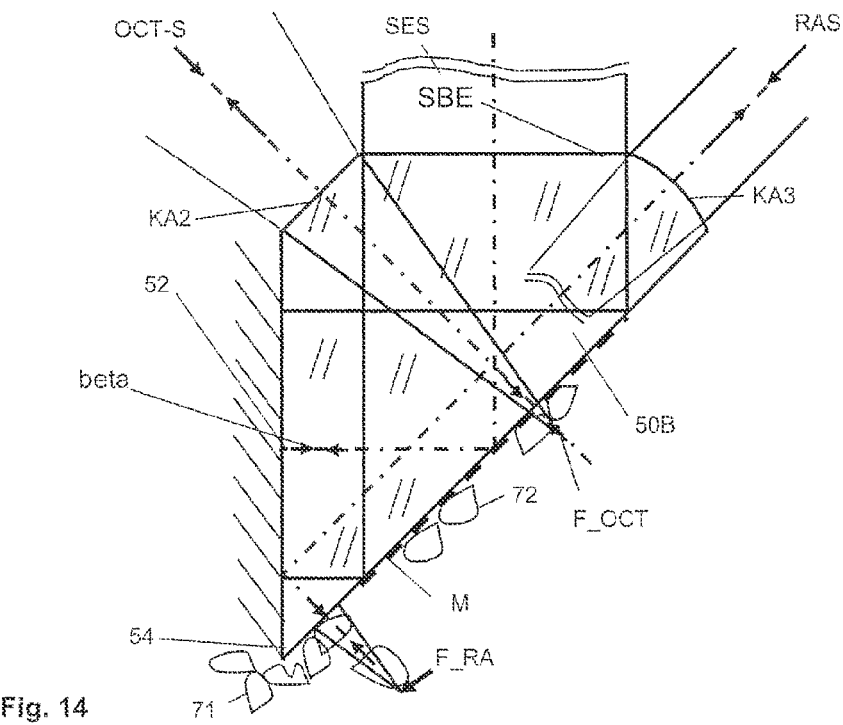

FIG. 14 shows another exemplary ATR prism 50B (for example a diamond ATR prism) configured to serve as an optical coupling element for spectroscopic ellipsometry, Raman spectroscopy and optical coherence tomography measurements. The ATR prism 50B of this example generally corresponds to the ATR prism 50B shown in FIG. 13 with the difference that the coupling surface KA3 in the optical path RAS of the Raman spectroscopy is a curved surface with an optical power.

Figure 15:
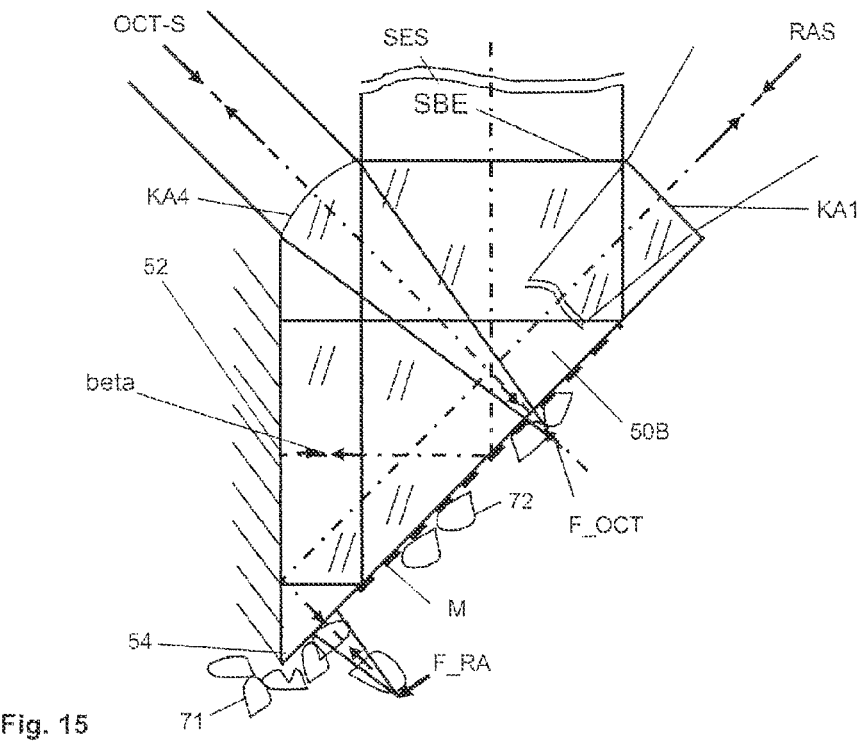

FIG. 15 shows another exemplary ATR prism 50B (for example a diamond ATR prism) configured to serve as an optical coupling element for spectroscopic ellipsometry, Raman spectroscopy and optical coherence tomography measurements. The ATR prism 50B of this example generally corresponds to the ATR prism 50B shown in FIG. 13 with the difference that the coupling surface KA4 in the optical path OCT-S of the optical coherence tomography (in particular swept source spectral domain optical coherence tomography) is a curved surface with an optical power.

Figure 16:
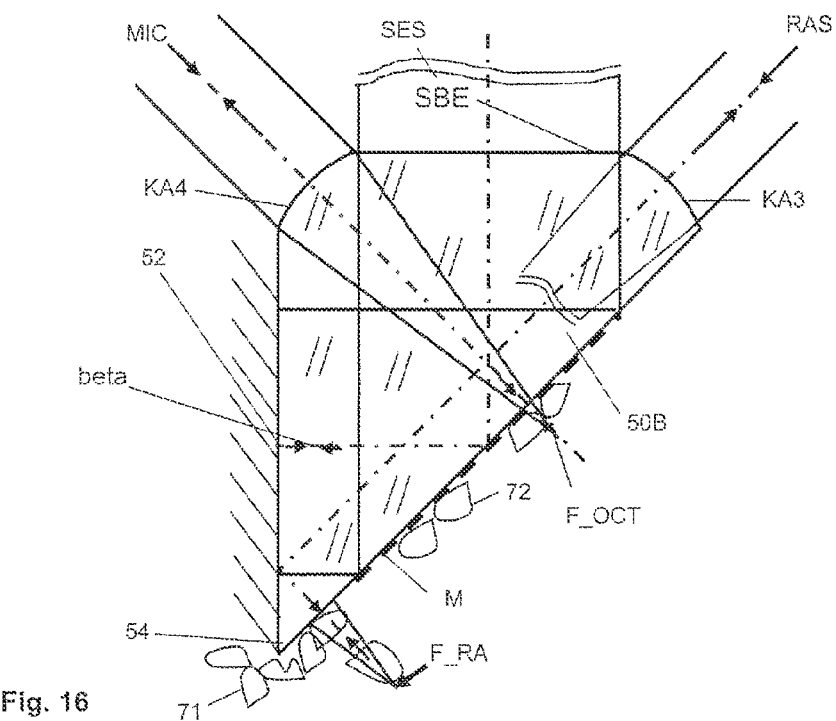

FIG. 16 shows another exemplary ATR prism 50B (for example a diamond ATR prism) configured to serve as an optical coupling element for spectroscopic ellipsometry, Raman spectroscopy and microscopy measurements or observations. The ATR prism 50B of this example generally corresponds to the ATR prism 50B shown in FIG. 13 with the difference that instead of a coupling surface for optical coherence tomography, the ATR prism has a coupling surface for microscopic observations. Further both the coupling surface KA3 in the optical path RAS of the Raman spectroscopy and the coupling surface KA4 in the optical path MIC of the microscopic observations are curved surfaces with an optical power.

In all of the examples shown in FIGS. 13 to 16, the ATR prism 50B is arranged such that the angle of incidence of the main ray of the light beam for Raman spectroscopy and/or optical coherence tomography and/or microscopic observations at the measuring portion is zero or near zero. Preferably, the angle of incidence is lower than 12°, for example several angular degrees. One or more of the optical coupling surfaces KA1 to KA4 may be a plane or a curved surface, for example a convex curved surface to introduce optical power in the respective optical path. The employment of a curved optical coupling surface may be advantageous, in particular in terms of miniaturization of the optical path for the Raman spectroscopy, optical coherence tomography, in particular swept-source spectral-domain OCT or microscopy.

Figure 17A:
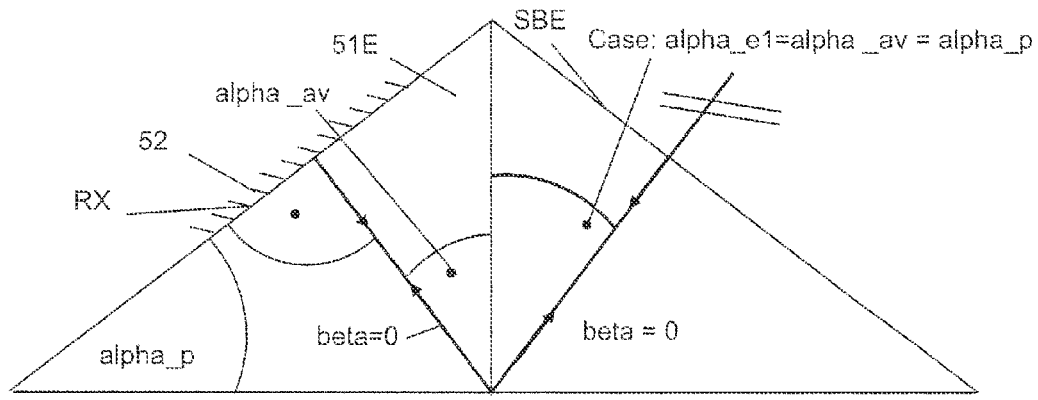
FIGS. 17A to 17C illustrate the invariance of the average angle alpha_av from the individual incidence angles.
Figure 17B:
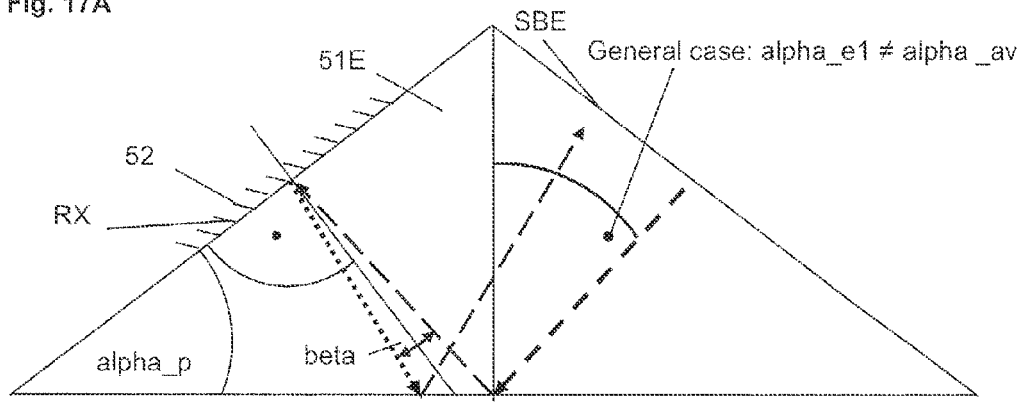
Figure 17C:
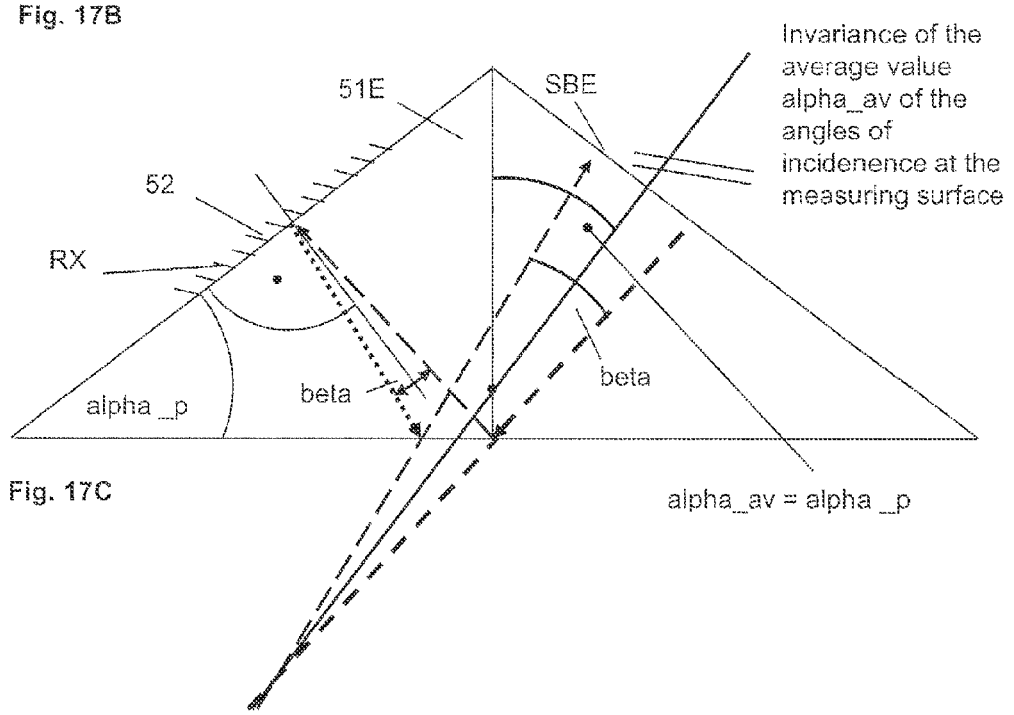

FIG. 17A to 17C illustrate the invariance of the average value apha_av of the magnitude of the incident angles of the main ray of the light beam striking the measuring portion M prior to and after undergoing a reflection at the reflective portion RX with respect to the individual incident angles alpha_e1 and alpha_e2. The ATR prism is a monolith element with a fixed prism angle alpha_p between the measuring surface and the reflective surface (more specifically between the measuring portion M and the reflective portion RX).

FIG. 17A illustrates the special case of normal incidence on the reflective portion RX of the reflective surface, wherein the angle of incidence (beta/2) of the attenuatedly totally reflected light beam on the reflective surface RX is zero. In this case the angle beta between the incoming light beam and the exit light beam is equal to zero (beta=0).

FIG. 17B illustrates the general case of light incidence on the reflective portion of the reflective surface at angles different from the angle of normal (perpendicular incidence). In this case, the angle of incidence beta/2 of the light beam on the reflective portion RX of the reflective surface is different from zero and alpha_e1≠alpha_av.

FIG. 17C illustrates the invariance of the average value alpha_av with respect to the individual incidence angles alpha_e1 and alpha_e2. The average value alpha_av is always equal to alpha_p (alpha_av=alpha_p), i.e. is invariant with respect to the individual angles of incidence alpha_e1 and alpha_12. This result in a high level of stability and robustness of the spectroscopic ellipsometric measurements.

Figure 18:
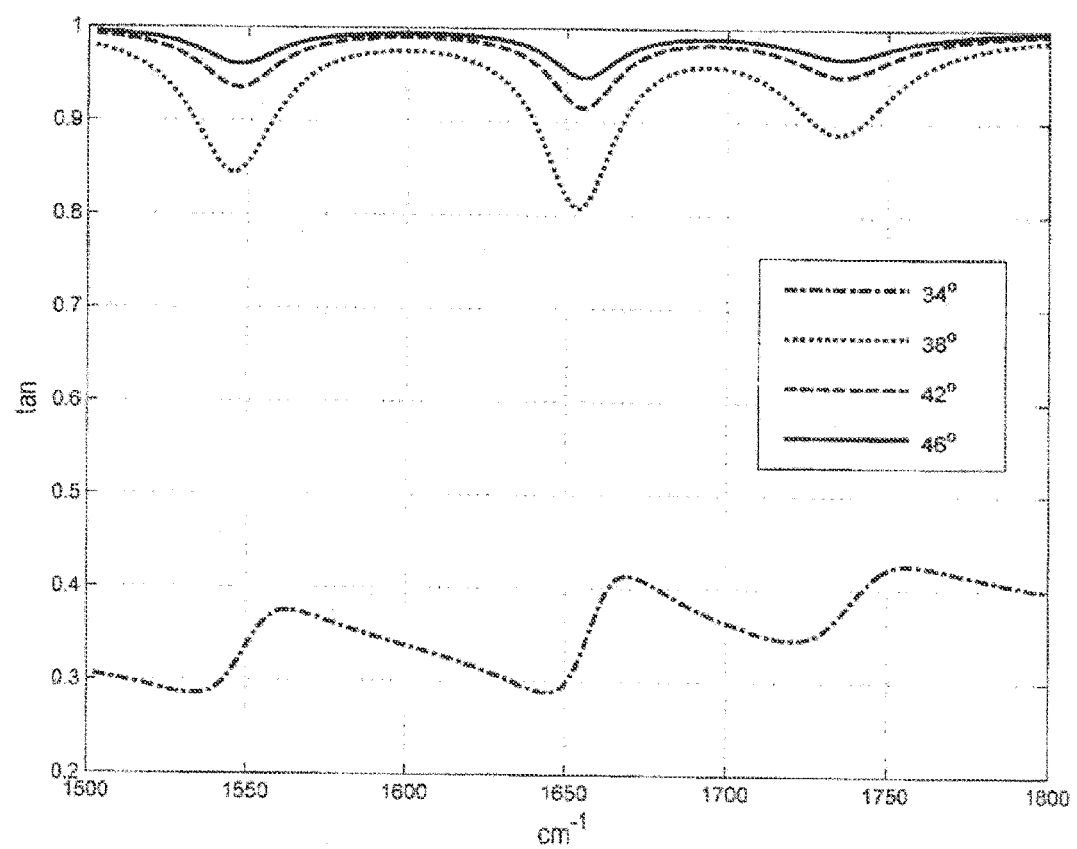
FIG. 18 shows the dependency of the ellipsometric parameter tangent Psi as a function of the wavenumber for different incident angles on the measuring part of the measuring surface.
Figure 19:
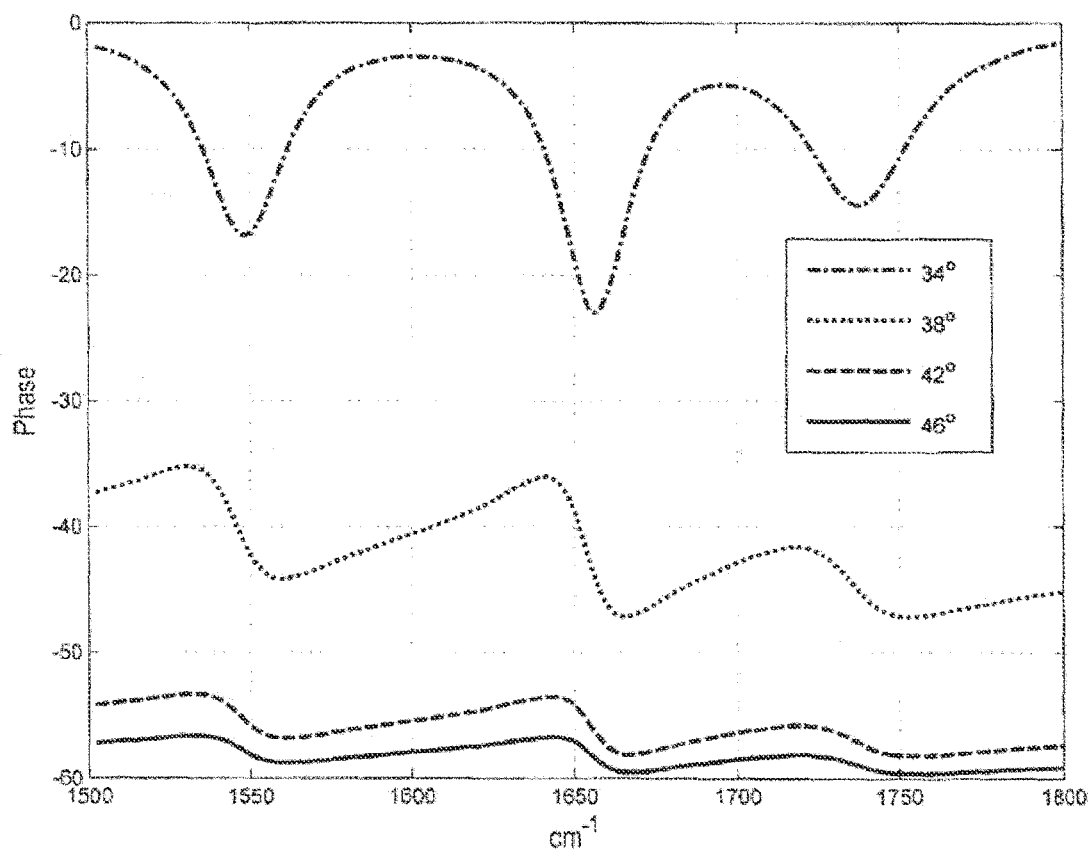
FIG. 19 shows the dependency of the phase difference Delta as a function of the wavenumber for different incident angles on the measuring part of the measuring surface.

FIG. 18 shows a simulation of the ellipsometric parameter tangent Psi (square root of the intensity ratio) as a function of the wavenumber for a human tissue sample at different angles of incidence alpha_e at the measuring portion M of the measuring surface (alpha_e=34°, 38°, 42° und 46°). FIG. 19 shows a simulation of the phase difference Delta as a function of the wavenumber for the same human tissue sample at different angles of incidence alpha_e (alpha_e=34°, 38°, 42° und 46°) on the measuring portion M of the measuring surface. The refractive index of the ATR prism is 2.4 (diamond) and the refractive index of the human tissue sample is assumed to be 1.4 (this is an approximate value). The modulations exhibited by each of the ellipsometric parameters tangent Psi and Delta are relatively high around the critical total reflection angle (in this case 35.6853°).

The optimal angle of incidence on the measuring portion for an attenuated total reflection may be experimentally determined for different type of measured objects, for example different tissue types. Dependent on the determined angle of incidence, the optimal value of the prism angle alpha_p may be determined. Further, the incident angles alpha_e1 und alpha_e2 at the measuring surface may be selected such as to be slightly greater or slightly smaller (for example several angular degrees) than the critical total reflection angle.

Figure 20:
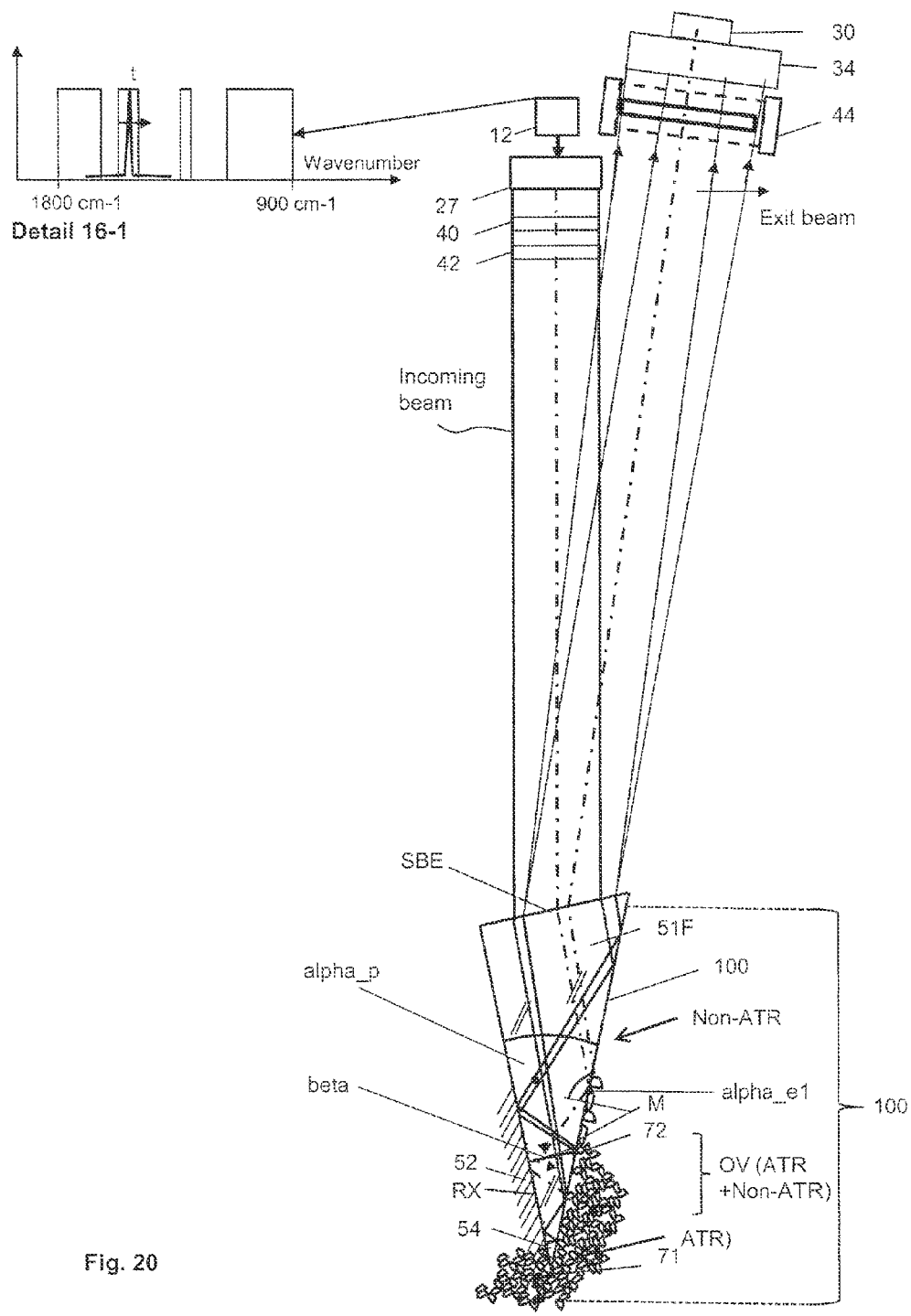
FIGS. 20 to 22 shows exemplary apparatuses for infrared spectroscopic ellipsometry.

FIG. 20 shows schematically the optical layout of an apparatus for infrared spectroscopic ellipsometry for cancer and/or metabolism diagnosis according to another example. The spectroscopic ellipsometer may be any of the described spectroscopic ellipsometers with the difference that it uses an ATR prism 51F made of crystalline silicon (Si) having a high refractive index n=3.4 in infrared. Crystalline silicon has a high hardness and is biocompatible. Further, due to the high refractive index, ATR prisms with very sharp cutting blades having cutting angles of less than 30° may be provided. Such small cutting angles considerably improve the cutting through the measured object (for example a human organ). As explained above, the cutting function may be optionally further improved by subjecting the ATR prism 51F to microvibrations (for example ultrasonic vibrations).

Further, due its high refractive index, a crystalline silicon surface behaves almost as a perfect mirror when the angle of incidence to the surface is greater than 60°, save for a phase difference delta from approximately 55° (which may be taken into account in the ellipsometric measurement). At such high incidence angles, total reflection without attenuation may be achieved. The mirror-like, non-attenuated total reflection may be advantageously used to guide incoming light coupled to the ATR prism 51F to a measuring portion M of a measuring surface in optical contact with the measured object 72 (for example freshly cut human tissue).

The ATR prism 51F may be arranged such that the light beam strikes the measuring surface at a plurality of regions or parts under different angles of light incidence. The ATR prism 51F may be configured such that in the upper part (identified as non-ATR in the figures), the light is incident at a high angle (for example about 60°), so that only non-attenuated total reflection occurs. In the lower part (identified as ATR in the figures), the light is incident at an angle at which attenuated total reflection occurs (for example, for a ATR prism made of crystalline silicon this angle is about 25°). The lower part of the measuring surface is in optical contact with the measured object 72 (e.g. freshly cut human tissue), so that information about the measurement object may be obtained by means of attenuated total reflection. In the middle part OV (overlapping region), both attenuated and non-attenuated total reflection occur. The diameter of this overlapping region depends for example on the incident angle alpha_e1. In the example shown in FIG. 20, the middle part OV (i.e. the overlapping region) of the total reflection with and without attenuation) has a diameter of approximately 1 mm.

It is possible to advantageously use of the overlapping region OV to construct ATR prism with very small size (with respect to the thickness and the cross-sectional dimensions). For example, the cross-sectional size of the ATR prism may be reduced to match the size of the light beam. The light beam may be slightly focused, so that the angular spread of the light beam may be made as small as a few angular degrees. This enables forming an almost diffraction-limited spot of infrared light on the measuring surface and the miniaturization of the ATR prism and the measuring probe.

Due to the use of a miniaturized prism exhibiting nearly diffraction limited optical design, the damages to measured object (for example human organ or tissue) may be reduced, which makes the ATR prism particularly advantageous for in-vivo measurements in living organs.

More specifically, the spectroscopic ellipsometer shown in FIG. 20 comprises an infrared light source 12 in combination with a variable wavelength (for example a swept source type) light source, such as a quantum cascade light battery. Preferably individual spectral bands may be selected for performing the spectroscopic ellipsometric measurements. Detail 16-1 shows the spectrum of the emitted light. The light emitted from the light source is coupled into an optical system for adjustment of the beam's cross section 27, passes through a polarizer 40 and a retarded 42 and is coupled to the ATR prism 51F via the optical coupling surface SBE.

The ATR prism 51F is made of a crystalline silicon and has a plate-like form. The ATR prism 51F comprises an optical coupling surface SBE (a plane surface), a measuring surface 100 having a measuring portion M and a reflective surface having a reflective portion RX formed by a reflective layer 52. The reflective surface and the measuring surface intersect, thereby forming a cutting blade 54. The prism angle alpha_p (which is also the angle of the cutting blade 54) is smaller or equal to 30°.

After passing through the optical coupling surface SBE, the incoming light strikes the upper part of the measuring surface 100 at an angle higher than 60° and is totally reflected. At such high incidence angle the measuring surface 100 behaves like an almost perfect mirror and the total reflection is not attenuated (non-ATR). Accordingly, it is not necessary to employ additional reflective layer at this part, which reduces the costs of the optical system. Further, the ATR prism 51F is configured and arranged such that the angle of incidence at the measuring part M of the measuring surface 100 (including in particular the lower part ATR) is about 25°. At this incident angle, an attenuated total reflection is possible that may be advantageously used to obtain data about the measured object 72 in optical contact with the measuring surface 100 at this part.

The ATR prism 51F is so inclined, that at a prism angle alpha_p (angle between the measuring surface 100 and the reflective surface) of about 25°, a good coupling of the incoming and decoupling of the exit light beam is possible.

After undergoing a double attenuated total reflection the light is guided out of the ATR prism by means of staggered reflections on the reflective surface and the non-ATR portion of the measuring surface. The exit light beam enters a detection path comprising an analyzer positioned on a rotary stage 44 and a detector 30 together with its optical system 34.

Figure 21:
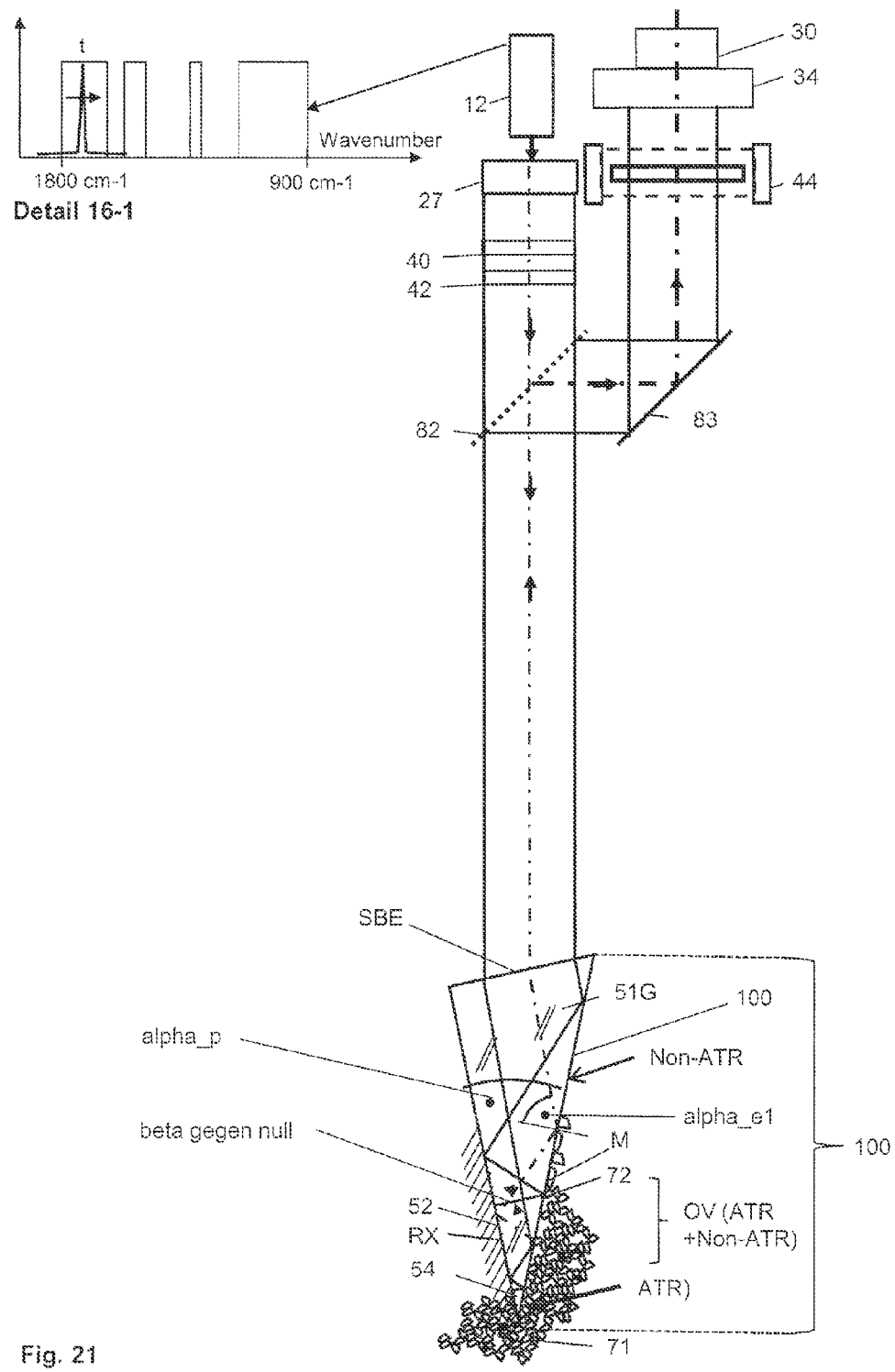

FIG. 21 shows schematically the optical layout of an apparatus for infrared spectroscopic ellipsometry for cancer and/or metabolism diagnosis according to another example, similar to the one shown in FIG. 20. The ATR prism 51G is made of crystalline silicon, has a prism angle of approximately 25° and is similar to the ATR prism 51F shown in FIG. 20. In FIG. 21 the ATR prism 51G is arranged such that the incoming light and the exiting light follow generally the same optical path (i.e. the incoming light beam and the exit light beam are collinear). The two beams are separated by means of a beam splitter 82 and a mirror 83.

Figure 22:
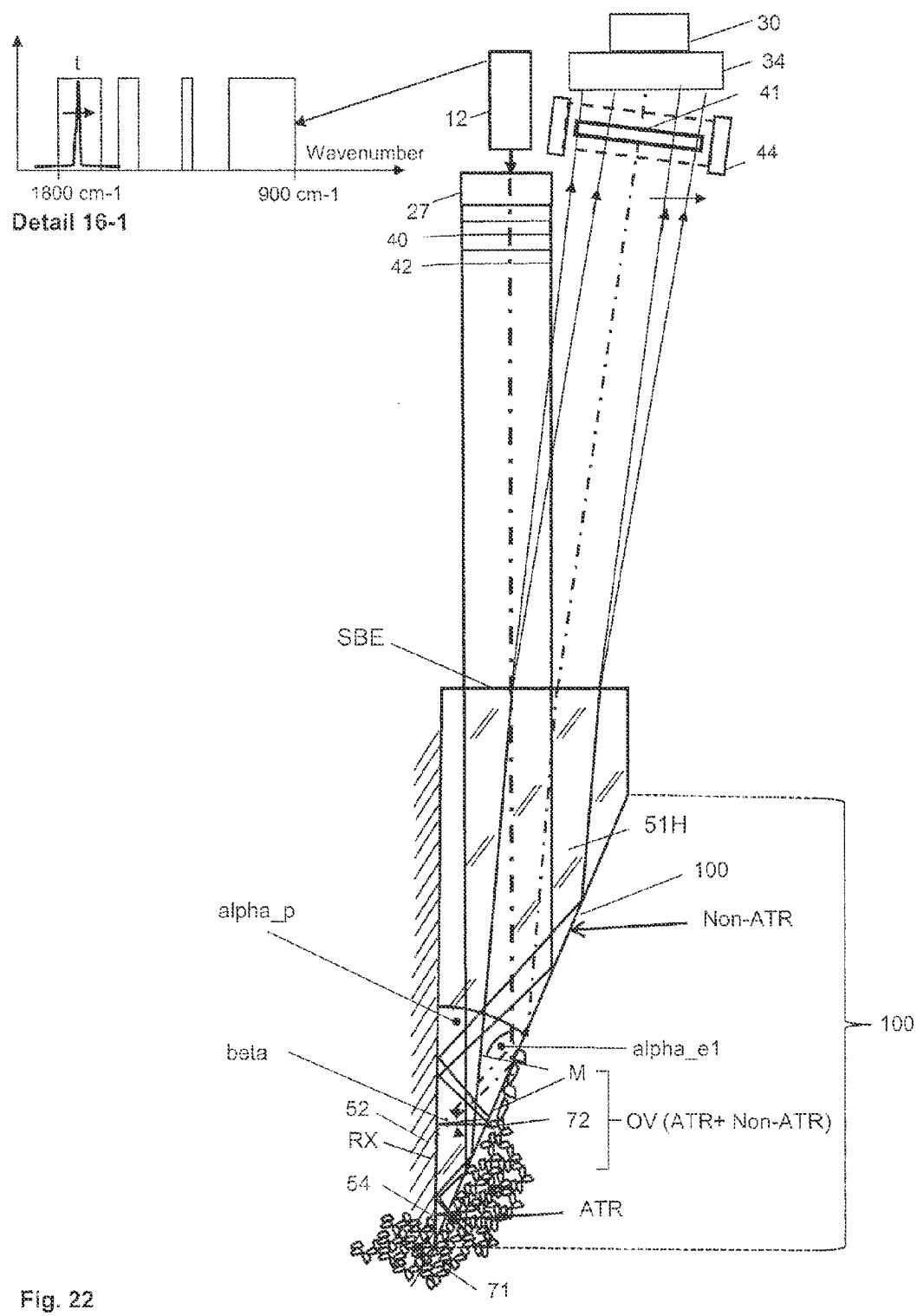

FIG. 22 shows schematically the optical layout of an apparatus for infrared spectroscopic ellipsometry for cancer and/or metabolism diagnosis according to another example, similar to the one shown in FIG. 20. The ATR prism 51H in this example has a plate form and is made of a crystalline germanium, produced for example by a zone melting, zone refining or floating zone process. As the refractive index of crystalline germanium (n=4) is higher than the refractive index of crystalline silicon, the prism angle (and respectively the cutting angle) may be reduced to for example about 20° to 22° (the critical total reflection angle for human tissue with reference index of about 1.4 is about 20.5°). The small prism angle (cutting blade angle) improves the insertion of the probe in the measured object and respectively cutting through the object. Further, there is no need to apply a reflective layer on the measuring surface to the measuring surface. However, the crystalline germanium has a lower hardness than crystalline silicon and it may be less biocompatible.

The ATR prism 51H is arranged such that the main ray of the incoming light beam is incident at the optical coupling surface SBE perpendicularly (normally). This arrangement reduces the angular spread due to dispersion may be reduced. Nevertheless, a small angular beam spread may still be present.

In the examples shown in FIG. 21 and FIG. 22, the ATR prism is made of a high refractive index optical material such as silicon (n=3.4) or germanium (n=4). However, the effect of non-attenuated total reflection at high incident angles may be also be advantageously used in ATR prisms of other high refractive index materials, such as diamond, KRS5 or ZnSe. In such prisms there may also be an overlapping region OV on the measuring surface M where both non-attenuated and attenuated total reflection occur. Further, the measuring surface may be arranged such that light is incident on different regions or parts of the measuring surface at different angles, with the angle of light incidence at some regions being considerably higher than the angle of incidence on other regions. Accordingly, the measuring surface of the ATR prism may (optionally) exhibit at least one region in which non-attenuated total reflection occurs, at least one region in which attenuated total reflection occurs, and at least one overlapping region in which both non-attenuated and attenuated total reflection occur. The (optional) non-attenuated total reflection region may be used to guide the light beam through the prism, and the overlapping and the attenuated total reflection regions may be used to obtain information about the measured object. As disclosed above, this allows the construction of ATR prisms with very small size. Due to the use of miniaturized prisms exhibiting nearly diffraction limited optical design, the damages to measured object (for example human organ or tissue) may be reduced, which makes the ATR prism particularly advantageous for in-vivo measurements in living organs.

Figure 24:
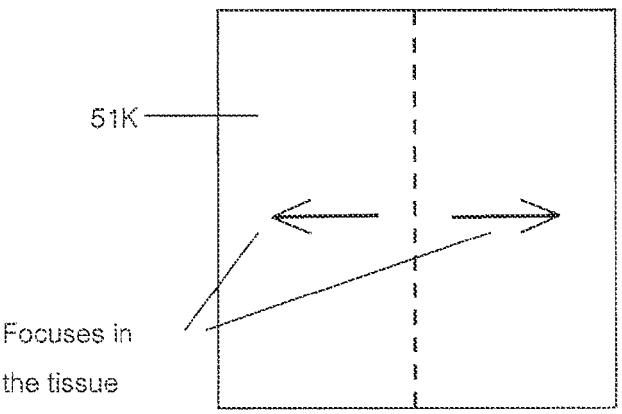
FIG. 24 is a view from below of the multi-channel ATR prism shown in FIG. 23.

It is further possible to construct ATR prisms having a plurality of measuring channels for spectroscopic ellipsometric measurements. One exemplary multi-channel ATR prism is shown in FIGS. 23 and 24.

Figure 23:
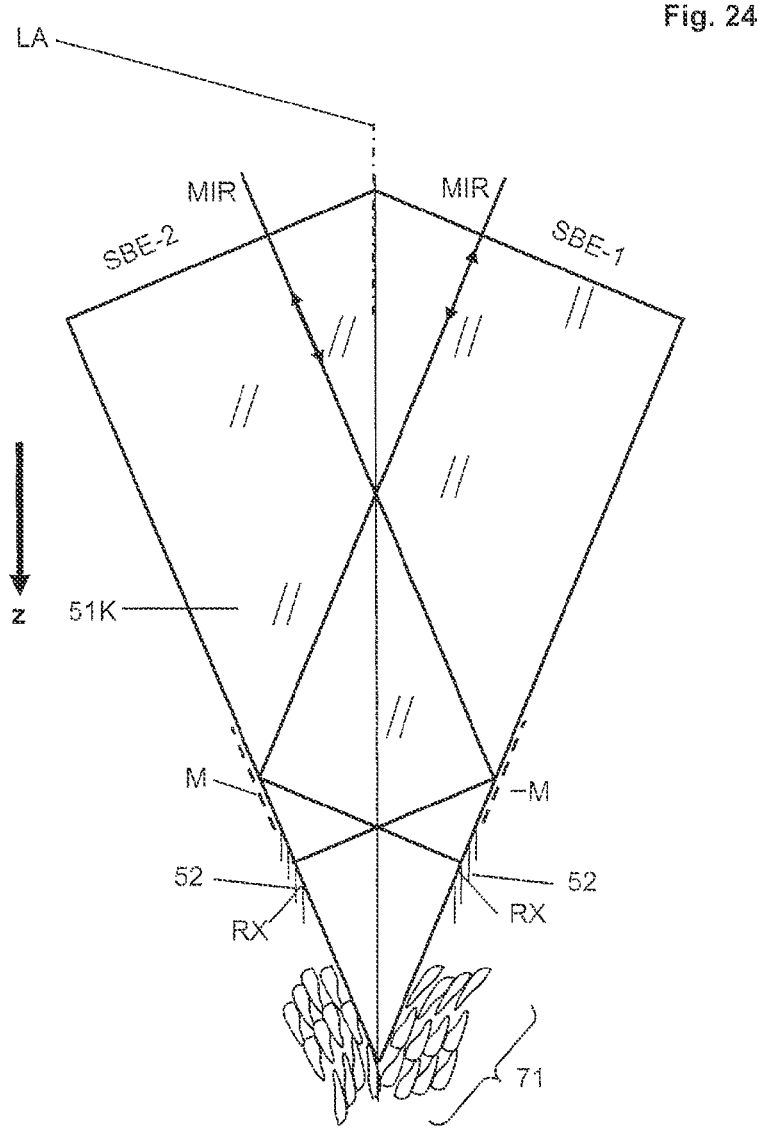
FIG. 23 shows an exemplary multi-channel ATR prism.

FIG. 23 shows an ATR prism 51K with two measuring channels. FIG. 24 shows a view from the bottom (from the tip side) of the ATR prism shown in FIG. 23.

The ATR prism 51K has a pyramid form having a longitudinal axis LA. The ATR prism 51K comprises two optical coupling surfaces SBE-1 and SBE-2 for coupling infrared light in the prism and decoupling infrared light out of the ATR prism 51K, each optical coupling surface being assigned to a different measuring channel. The ATR prism 51K comprises further a first side surface and a second side surface intersecting with each other and forming a double sided cutting blade at the tip of the pyramid. The first and the second side surfaces each have a measuring portion M that is in optical contact with the measured object (e.g. freshly cut tissue) and a reflective part RX formed by a reflective layer 52. Light passing through the optical coupling surface SBE-1 undergoes an attenuated total reflection at the measuring portion M of the first side surface, is reflected back by the reflective portion RX of the second side surface towards the first side surface, strikes again the measuring portion M of the first side surface and undergoes a second attenuated total reflection to thereby form a first exit light beam (first measuring channel). Similarly, light passing through the optical coupling surface SBE-2 is totally reflected by the measuring portion M of the second side surface, reflected by the reflective portion RX of the first side surface back towards the second side surface, strikes the measuring portion M of the second side surface and is totally reflected to thereby form a second exit light beam (second measuring channel). Each of the first and second side surfaces serves both as a measuring surface and as reflective surface.

Thus it is possible to perform simultaneously two measurements on two sides of the ATR prism. At least a portion of the remaining components of the spectroscopic ellipsometer, such as polarizer 40, retarder 41, analyzer 42, etc. can be used for both measuring channels. There may be, however, provided two infrared detectors for each measuring channels.

In the example shown in FIGS. 23 and 24, the prism has a two-sided pyramid form. Generally, the ATR prism may have more than two sides, for example be a 4-sided, 6-sided, etc. pyramid. Accordingly, there may be a corresponding number of measuring channels for simultaneously carrying out a plurality of spectroscopic ellipsometric measurements (n=2, 4, etc.). Generally, the ATR prism may have even number of sides and respective even number of measuring channels.

In the above examples, the detected spectroscopic ellipsometry data may be processed to obtain one or more ellipsometric parameters as a function of the wavelength (or wavenumber). Based on the obtained ellipsometric parameters, it is possible to determine the refractive index "n" and the absorption coefficient "k" (i.e. the complex refractive index) of the measured object, such as human tissue. Preferably, this is done in a real time or quasi-real time (for example is several minutes or less), for example during a surgical intervention. Based on these data, it is possible to carry out a comparison with reference data of the refractive index and absorption coefficient of known objects. An unknown measured object may be then identified or classified in predetermined categories. For example tissue samples of different organs in different states (healthy, malign, etc.) examined previously by means of hystopathological analysis may be used to obtain reference data which may be used to classify the freshly cut tissue sample, for example during a surgery.

To be noted further is that in the middle infrared range, due to diffractive effects, the quality with which light beams may be collimated is lower than in the visible range. Thus, the light beam striking the ATR prism (incoming light beam) generally exhibits certain angular spread. However, the angular spread may be reduced considerably due to the high refractive index of the diamond, ZnSe, silicon or germanium. This applies to all examples shown in FIGS. 1 to 24.

The computational aspects described here can be implemented in digital electronic circuitry, or in computer hardware, firmware, software, or in combinations of them. When appropriate, aspects of these systems and techniques can be implemented in a computer program product, for example tangibly embodied in a machine-readable storage device for execution by a programmable processor; and method steps can be performed by a programmable processor executing a program of instructions to perform functions by operating on input data and generating an output.

To provide for interaction with a user, a computer system can be used having a display device, such as a monitor or a LCD screen for displaying information to the user and a keyboard, a pointing device such as a mouse or a trackball, a touch-sensitive screen, or any other device by which the user may provide input to computer system. The computer system can be programmed to provide a graphical user interface through which the computer program(s) interact(s) with the user.

A number of embodiments have been described. Nevertheless, it will be understood that various modifications may be made. For example, the steps described can be performed in a different order and still achieve desirable results. Further, various elements disclosed in connection with a given example (such as for example the ATR prisms, the illumination and detection paths) may be combined with elements of other examples. Accordingly, other embodiments are within the scope of the claims.

TABLE 1

List of Reference Numerals with Descriptors:

| Reference numeral | Description |
|---|---|
| alpha_e1 | Angle of incidence of the light beam incident on the measuring portion of the measuring surface of the ATR prism prior to a reflection by the reflective portion of the reflective surface. The angle alpha_e1 is the angle between the main ray of the light beam incident on the measuring portion and the normal to the measuring portion. |
| alpha_e2 | Angle of incidence of the light beam incident on the measuring surface after a reflection by the reflective portion of the reflective surface. The angle alpha_e2 is the angle between the main ray of the reflected light beam incident on the measuring portion and the normal to the measuring portion. |
| alpha_p | Angle between the measuring portion of the measuring surface and the reflective portion of the mirror surface of the ATR-probe (prism angle) |
| alpha_av | Average value of the magnitudes of the two angles of incidence on the measuring portion of the measuring surface alpha_e1 and alpha_e2 (alpha_av = (alpha_e1 + alpha_e2)/2) |
| beta | Angle between the main ray of the light beam incident on the measuring surface of the ATR prism and the main ray of the exiting beam (i.e. the beam leaving the ATR prism after double total reflection at the measuring surface). The angle is twice the angle of incidence at the reflective portion of the reflective surface. |
| beta/2 | Angle of incidence at the reflective portion of the reflective surface of the ATR-prism. |
| ATR | Attenuated Total Reflection/Area of attenuated total reflection |
| Non-ATR | Non-Attenuated Total Reflection/Area of non-attenuated total reflection |
| OV | Overlapping area of attenuated and non-attenuated total reflection |
| LA | Longitudinal axis of the probe |
| gamma | The angular beam spread due to dispersion |
| M | Measuring portion of the measuring surface of the ATR prism |
| RX | Reflective portion of the reflective surface of the ATR prism |
| KA1 | Optical coupling surface of the ATR prism |
| KA2 | Optical coupling surface of the ATR prism |
| KA3 | Optical coupling surface of the ATR prism |
| KA4 | Optical coupling surface of the ATR prism |
| MIC | Microscopic optical path |
| SBE | Optical coupling surface of the ATR prism for the spectroscopic ellipsometry measurement |
| SES | Spectroscopic ellipsometry beam path (Spectroscopic ellipsometry beam path |
| F_RA | Focus of the Raman excitation light |
| F_OCT | Focus of the OCT measuring light |
| MS | Micro-vibrations of the ATR prism |
| oB | Upper part of the optical arrangement shown in FIG. 12 |
| OCT-S | OCT beam path (OCT measurement path) |
| RAS | Raman spectroscopy beam path (Raman spectroscopy measurement path) |
| uB | Lower part of the arrangement shown in FIG. 12 |
| 10 | Measuring probe |
| 11 | Infrared beamline of a synchrotron |
| 12 | Broadband light source emitting monochromatic or quasi-monochromatic light with a variable (scannable) wavelength, for example quantum cascade laser battery (optionally with a collimator output) |
| 15 | Laser (for example quantum cascade laser) |
| 20 | Broadband light source emitting light with continuous or quasi-continuous spectrum (for example a quantum cascade laser battery, optionally exhibiting an infrared fiber output). |
| 21 | Monochromator |

TABLE 1-continued

List of Reference Numerals with Descriptors:

| Reference numeral | Description |
|---|---|
| 22 | Fiber based optical coupling system with a collimator output for beam expansion |
| 23 | Fiber based optical coupling system with a collimator output for beam expansion |
| 23A | Fiber based optical coupling system |
| 24 | Silver-halide fiber |
| 25 | Hyperspectral modulator |
| 27 | Optical system for adjustment of the beam's cross section |
| 29 | Stainless steel sheathing/housing |
| 30 | Infrared detector |
| 31 | Reference detector (e.g. a mercury-cadmium telluride (MCT) detector). |
| 32 | Optical system of the reference detector |
| 33 | Optical system of the detector (e.g. fiber based) |
| 34 | Optical system of the detector |
| 35 | Collimator lens |
| 36 | Focusing lens |
| 40 | Polarizer |
| 41 | Analyzer (rotatable) |
| 42 | Retarder (Compensator) |
| 44 | Rotary stage, preferably computer controlled |
| 50 | ATR prism |
| 50A | ATR prism |
| 50B | ATR prism |
| 51A | ATR prism (e.g. a diamond ATR prism) |
| 51B | ATR prism (e.g. a diamond ATR prism) |
| 51C | ATR prism (e.g. a diamond ATR prism) |
| 51D | ATR prism (e.g. a diamond ATR prism) |
| 51E | ATR prism (e.g. a diamond ATR prism) |
| 51F | ATR prism (e.g. a crystalline silicon ATR prism) |
| 51G | ATR prism (e.g. a crystalline silicon ATR prism) |
| 51H | ATR prism (e.g. a crystalline silicon ATR prism) |
| 51K | ATR prism having multiple measuring and reflective surfaces (2-channel ATR prism) |
| 52 | Reflective layer (may have a multilayer structure, preferably with hard coating outermost layer) |
| 52A | Reflective layer (may have a multilayer structure, preferably with hard coating outermost layer) |
| 52B | Reflective layer (may have a multilayer structure, preferably with hard coating outermost layer) |
| 53 | Cutting blade of the ATR prism |
| 54 | Cutting blade of the ATR prism |
| 55 | Optical component for adjusting the cross sectional of the incident optical beam (for example mirror-based). |
| 56 | Optical component for adjusting the cross sectional of the output optical beam (for example mirror-based) |
| 57 | First off-axis parabolic mirror |
| 58 | Second off-axis parabolic mirror |
| 59 | Mirror |
| 60 | Computer controlled drive system (e.g. a computer controlled translational or linear stage) |
| 61 | Computer controlled drive system (e.g. a computer controlled, balanced drive system (e.g. a computer controlled rotational stage) |
| 63 | Beam splitter plate (e.g. from ZnSe) |
| 64 | Beam splitter layer (e.g. adapted for the MIR spectral range) |
| 65 | Rotary stage for alignment of the optical system |
| 66 | Triple-mirror type reflector (e.g. hollow cube reflector) |
| 67 | Roof-edge type mirror |
| 68A | Translational mirror based Interferometer employing triple mirrors |
| 68B | Rotating mirror based Interferometer with triple reflectors |
| 69 | A single-side metal reflective coating (e.g. aluminum reflective coating) |
| 70 | Blazed diffractive grating |
| 71 | Uncut human soft tissue |
| 72 | Cut human soft tissue in close contact with the measuring portion |
| 73 | Stomach tissue undergoing surgical operation |
| 74 | Surface of the organ to be examined |
| 82 | Beam splitter |
| 83 | Mirror |
| 91 | Raman excitation laser |
| 92A | Monomode fiber in the illumination path |

TABLE 1-continued

List of Reference Numerals with Descriptors:

| Reference numeral | Description |
|---|---|
| 92B | Monomode fiber outside of the measuring probe, arranged downstream of the Y fiber coupler |
| 92C | Monomode fiber within the ATR probe |
| 92D | Monomode fiber in the detection path |
| 93 | Y fiber coupler |
| 94 | Notch-Filter |
| 95 | Optical transfer system |
| 96 | Fourier spectrometer for a scattered Raman light |
| 100 | Measuring surface |
| 101 | Source and Fourier spectrometer assembly |
| 102 | Fiber based optical coupling for a plurality of measuring probes |
| 103 | Kit of measuring probes |
| 104 | Detector assembly |

We claim:

1. An apparatus for spectroscopic ellipsometry, preferably for infrared spectroscopic ellipsometry, comprising:
   a light source;
   a detector;
   a polarizer;
   an analyzer; and
   a measuring probe comprising:
      an attenuated total reflection (ATR) prism having at least a first surface having at least one measuring portion configured to be brought in optical contact with a measured object, and at least a second surface having at least one reflective portion,
      the ATR prism being configured such that:
         at least a portion of polarized light entering the measuring probe undergoes an attenuated totally reflection at the at least one measuring portion of the first surface,
         at least a portion of the totally reflected light is reflected back towards the first surface by the at least one reflective portion of the second surface, and
         at least a portion of the light reflected back by the at least one reflective portion of the second surface undergoes an attenuated total reflection at the at least one measuring portion of the first surface and is decoupled from the ATR prism,
      wherein a difference between a magnitude of an angle between the first surface and the second surface and a magnitude of a critical total reflection angle is less than a predetermined value.

2. The apparatus for spectroscopic ellipsometry according to claim 1, wherein the first surface and the second surface intersect along a common line of intersection to form a cutting blade for cutting through the measured object.

3. The apparatus for spectroscopic ellipsometry according to claim 2, wherein the cutting blade exhibits a cutting angle of less than or equal to 60°.

4. The apparatus for spectroscopic ellipsometry according to claim 1, wherein the ATR prism is made of a material comprising at least one of: a diamond, a crystalline silicon, and a crystalline germanium.

5. The apparatus for spectroscopic ellipsometry according to claim 1, wherein the measuring probe includes a longitudinal axis, and wherein the ATR prism is arranged at a first end of the measuring probe such that an angle between the first surface and the longitudinal axis of the measuring probe is equal to or less than 60°.

6. The apparatus for spectroscopic ellipsometry according to claim 1, wherein at least one of the first surface and the second surface comprises at least one reflective portion, configured to reflect incident light by means of non-attenuated total reflection towards the other surface of the ATR prism.

7. The apparatus for spectroscopic ellipsometry according to claim 1, wherein the first surface comprises a plurality of measuring portions.

8. The apparatus for spectroscopic ellipsometry according to claim 1, wherein the ATR prism further comprises a plurality of first surfaces, each first surface having at least one measuring portion configured to be brought in optical contact with a measured object.

9. The apparatus for spectroscopic ellipsometry according to claim 1, wherein the ATR prism further comprises:
   a first optical coupling surface for coupling light for spectroscopic ellipsometric measurement into the ATR prism; and
   a second optical coupling surface for coupling light for a further optical measurement into the ATR prism, the light for further optical measurement including at least one of: Raman excitation light, light for optical coherence tomography measurements, light for swept-source spectral-domain optical coherence tomography measurements, and light for microscopic observations.

10. The apparatus for spectroscopic ellipsometry according to claim 1, further comprising:
    a plurality of measuring probes, each measuring probe comprising an ATR prism, wherein each measuring probe has the same angle between the respective first surface and second surface.

11. The apparatus for spectroscopic ellipsometry according to claim 1, wherein
    the light source comprises a broad band light source emitting light with a substantially continuous spectrum, and wherein the apparatus further comprises at least one of a monochromator, a spectrometer, and an interferometer.

12. A method for spectroscopic ellipsometric measurement, the method comprising:
    bringing at least one measuring portion of a first surface of an attenuated total reflection (ATR) prism in optical contact with a measured object, wherein the ATR prism is a component of a measuring probe;
    illuminating the at least one measuring portion with incident light from a light source, such that at least a portion of the incident light undergoes an attenuated totally reflection at the at least one measuring portion;
    reflecting, by at least one reflective portion of a second surface of the ATR prism, at least a portion of the totally reflected light back towards the at least one measuring portion, wherein at least a portion of the light reflected back by the at least one reflective portion undergoes an attenuated total reflection at the at least one measuring portion of the first surface;
    decoupling the totally reflected light from the ATR prism
    detecting at least a portion of the light exiting the ATR prism; and
    determining at least one ellipsometric parameter as a function of the wavelength of the incident light.

13. The method for spectroscopic ellipsometric measurement according to claim 12, further comprising:
    relocating the measuring probe to a new region of the measured object;

bringing the at least one measuring portion in optical contact with the measured object;

illuminating the at least one measuring portion;

reflecting, by the at least one reflective portion of the second surface at least a portion of the totally reflected light back towards the measuring portion;

decoupling the totally reflected light from the ATR prism; and detecting at least a portion of the outgoing light.

14. The method for spectroscopic ellipsometric measurement according to claim 12, further comprising:

illuminating the at least one measuring portion of the first surface of the ATR prism with Raman excitation light, wherein the Raman excitation light is incident perpendicularly on the measuring portion;

detecting at least a portion of the Raman scattered light; and subjecting the detected light to a Raman spectroscopy analysis.

15. The apparatus for spectroscopic ellipsometry according to claim 1, wherein a difference between a magnitude of an angle between the first surface and the second surface and a magnitude of a critical total reflection angle is less than 12°.

16. The apparatus for spectroscopic ellipsometry according to claim 1, wherein the light source comprises a broadband light source emitting monochromatic or quasi-monochromatic light with a variable wavelength.

17. The apparatus for spectroscopic ellipsometry according to claim 1, further comprising:

a plurality of measuring probes, each measuring probe comprising an ATR prism, wherein the measuring probes have a different angle between respective first surfaces and second surfaces.

18. The method for spectroscopic ellipsometric measurement according to claim 12, further comprising:

illuminating the at least one measuring portion of the first surface of the ATR prism with Raman excitation light, wherein the Raman excitation light is at an angle deviating from a perpendicular incidence of the Raman excitation light on the measuring portion by no more than ±15°;

detecting at least a portion of the Raman scattered light; and subjecting the detected light to a Raman spectroscopy analysis.

19. The method for spectroscopic ellipsometric measurement according to claim 12, further comprising:

illuminating the at least one measuring portion of the first surface of the ATR prism with optical coherence tomography illumination light, wherein the optical coherence tomography illumination light is incident perpendicularly on the measuring portion;

detecting at least a portion of the light returned back from the measured object; and subjecting the detected light to an optical coherence tomography analysis.

20. The method for spectroscopic ellipsometric measurement according to claim 12, further comprising:

illuminating the at least one measuring portion of the first surface of the ATR prism with optical coherence tomography illumination light, wherein the optical coherence tomography illumination light is at an angle deviating from a perpendicular incidence of the optical coherence tomography illumination light on the measuring portion by no more than ±15';

detecting at least a portion of the light returned back from the measured object; and subjecting the detected light to an optical coherence tomography analysis.

21. The method for spectroscopic ellipsometric measurement according to claim 12, further comprising:

illuminating the at least one measuring portion of the first surface of the ATR prism with illumination light in a visible spectral range, wherein the illumination light is incident perpendicularly on the measuring portion; and detecting at least a portion of the light returned back by the measured object, thereby forming a microscopic image of the measured object.

22. The method for spectroscopic ellipsometric measurement according to claim 12, further comprising:

illuminating the at least one measuring portion of the first surface of the ATR prism with illumination light in a visible spectral range, wherein the illumination light is at an angle deviating from a perpendicular incidence of the illumination light on the measuring portion by no more than ±15°; and detecting at least a portion of the light returned back by the measured object, thereby forming a microscopic image of the measured object.

* * * * *